United States Patent
Zell et al.

(10) Patent No.: US 11,634,397 B2
(45) Date of Patent: Apr. 25, 2023

(54) PROCESS AND INTERMEDIATES FOR THE PREPARATION OF FLUENSULFONE

(71) Applicant: ADAMA MAKHTESHIM LTD., Beer Sheva (IL)

(72) Inventors: Thomas Zell, Beer-Sheva (IL); Shlomi Cohen, Beer-Sheva (IL)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 28 days.

(21) Appl. No.: 17/280,146

(22) PCT Filed: Sep. 26, 2019

(86) PCT No.: PCT/IL2019/051063
§ 371 (c)(1),
(2) Date: Mar. 25, 2021

(87) PCT Pub. No.: WO2020/065652
PCT Pub. Date: Apr. 2, 2020

(65) Prior Publication Data
US 2022/0002258 A1  Jan. 6, 2022

Related U.S. Application Data

(60) Provisional application No. 62/736,498, filed on Sep. 26, 2018.

(51) Int. Cl.
*C07D 277/36* (2006.01)
(52) U.S. Cl.
CPC ................... *C07D 277/36* (2013.01)

(58) Field of Classification Search
CPC .................................................. C07D 277/36
See application file for complete search history.

(56) References Cited

FOREIGN PATENT DOCUMENTS

WO  98/47884 A1  10/1998
WO  03/095401 A1  11/2003

OTHER PUBLICATIONS

Guangxiao Li et al., "Fluoroalkane thioheterocyclic derivatives and their antitumor activity", European Journal of Medicinal Chemistry, Elsevier, Amsterdam, NL, vol. 93, Feb. 20, 2015, pp. 423-430, XP029176782, ISSN: 0223-5234, DOI: 10.1016/J. EJMECH.2015.02.031 scheme 1, compounds 2c, 6, 7; reaction step iv.
International Search Report dated Dec. 18, 2019 for corresponding application PCT/IL2019/051063.

*Primary Examiner* — Shawquia Jackson
(74) *Attorney, Agent, or Firm* — Miles & Stockbridge P.C.

(57) ABSTRACT

The invention provides a process for preparing heterocyclic fluoroalkenyl sulfones and their thioether and sulfoxide precursors of the formula: $Cl-R-S(O)_n-(CH_2)_2-CF=CF_2$ (Formula I') wherein R is a heterocyclic five-membered aromatic ring and n is 0, 1 or 2, comprising a step of dehalogenation of a compound of the formula: $Cl-R-S(O)_n-(CH_2)_2-CFX^1-CF_2X^2$ (Intermediate B), wherein $X^1$ and $X^2$ are independently halogen atoms, to remove said $X^1$ and $X^2$ atoms. Also included are novel intermediate compounds.

35 Claims, 13 Drawing Sheets

PROCESS AND INTERMEDIATES FOR THE PREPARATION OF FLUENSULFONE

CROSS-REFERENCE TO RELATED APPLICATIONS

This application is a national stage filing under 35 U.S.C. § 371 of PCT/IL2019/051063, filed on Sep. 26, 2019 which claims priority to U.S. Application No. 62/736,498 filed on Sep. 26, 2018. The applications are incorporated herein by reference in their entirety.

Fluensulfone, a powerful nematicide belonging to the class of heterocyclic fluoroalkenyl sulfones, has the following chemical structure:

(I)

Fluensulfone [chemical name: 5-chloro-2-[(3,4,4-trifluoro-3-buten-1-yl)sulfonyl]thiazole] is commercially available on the market as an emulsifiable concentrate formulation. It was first reported in EP 1200418, Example 3, where it was prepared via the two-step synthesis depicted below:

(III)

(II)

(I)

It is seen that the synthesis consists of chlorination of a compound of Formula III {chemically named 2-[(3,4,4-trifluoro-3-buten-1-yl)thio]thiazole} to add a chlorine atom to the aromatic ring, followed by oxidation of the chlorine-bearing sulfide of Formula II to create the sulfonyl group, arriving at Fluensulfone. Thus, the direct precursor of Fluensulfone is the compound of Formula II. Its chemical name is 5-chloro-2-[(3,4,4-trifluoro-3-buten-1-yl)thio]thiazole. Hereinafter it is sometimes named "Intermediate C1".

The compound of Formula III that was used as a starting material according to EP 1200418 is known from an earlier publication, WO 86/07590. Example 16 of WO 86/07590 shows that 2-[(3,4,4-trifluoro-3-buten-1-yl)thio]thiazole is prepared by coupling 2-mercaptothiazole and 1,1,2-trifluoro-4-bromo-1-butene:

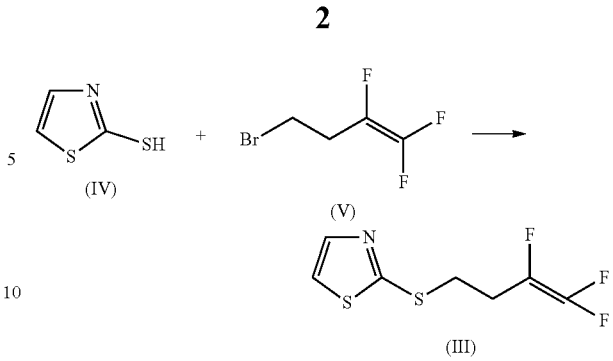

In fact, as shown in WO 86/07590, the mixed haloalkene of Formula V serves an important role in the formation of active heterocyclic fluoroalkenyl sulfones, because alkylation of the heterocyclic thiol (IV) with the haloalkene (V) directly incorporates the essential fluoroalkenyl functionality into the structure of the compound. For this reason, preparation of heterocyclic fluoroalkenyl sulfones reported in the prior art is often based on the mixed haloalkene of Formula V.

However, experimental work conducted in support of this invention indicates that the coupling of the heterocyclic thiol (IV) with the haloalkene (V) according to the scheme outlined above is performed prematurely, because the incorporation of the carbon-carbon double bond creates a site prone to chlorination, thus diverting the ring chlorination reaction that follows to unwanted by-products. Prior art-based synthesis for Fluensulfone suffers from drop in the yield owing to the unwanted side reaction.

DETAILED DESCRIPTION

Figure 1A:
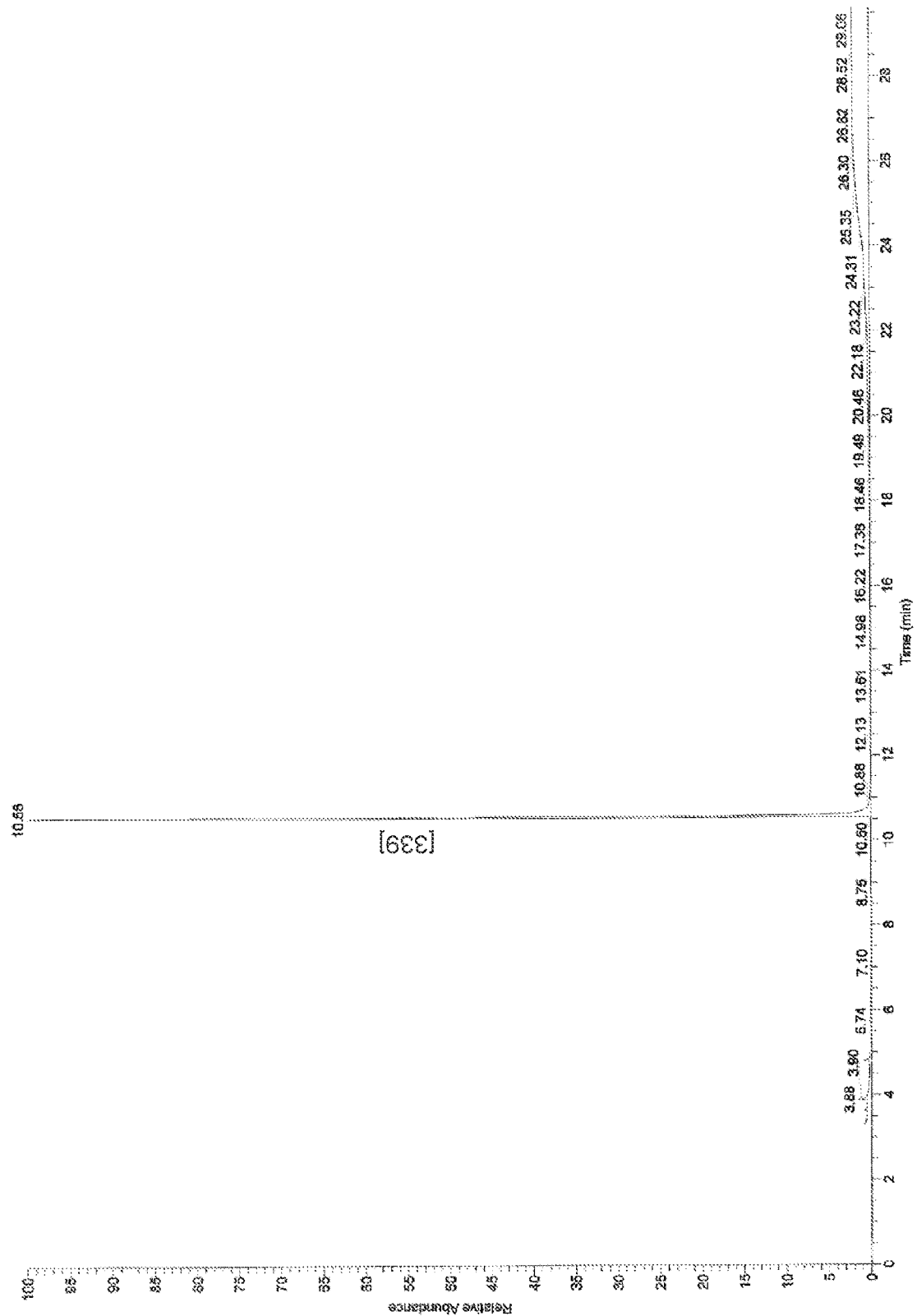
FIGS. 1A and 1B show chromatogram and mass spectrum, respectively, according to an example.

The inventors have now found that heterocyclic fluoroalkenyl sulfones bearing halogen atoms on the heterocyclic ring, such as Fluensulfone, are accessible via a synthetic pathway that does not require the use of the mixed haloalkene of Formula V. The alkylation of the heterocyclic thiol (IV) is achieved with the aid of a mixed haloalkane in lieu of the mixed haloalkene (V), for example, with 1,4-dibromo-2-chloro-1,1,2-trifluorobutane ($BrCH_2$—$CH_2$—$CFCl$—$CF_2Br$) to form the corresponding sulfide (thio-ether). The alkylation reaction is followed by chlorination, to attach a chlorine atom exclusively to the heterocyclic ring absent a competing carbon-carbon double bond. Only later the necessary carbon-carbon double bond is introduced to the molecule, through a dehalogenation (e.g., reduction) reaction that creates the terminal carbon-carbon double bond. As to the oxidation step that converts the sulfide to a sulfonyl group, it may take place either following the chlorination or the dehalogenation steps. It is of note that the oxidized form does not lend itself to chlorination. Hence the synthesis may be accomplished through routes that differ from one another in the order of steps; the chief requirement placed on the process is that the chlorination step precedes the dehalogenation (reduction) step. The alternative routes of the process, Route 1 and Route 2, are illustrated by the reaction scheme depicted below (where the aforementioned 1,4-Dibromo-2-chloro-1,1,2-trifluorobutane was used in the alkylation step of the 2-mercaptothiazole starting material), alongside Route 3 which failed on the chlorination step:

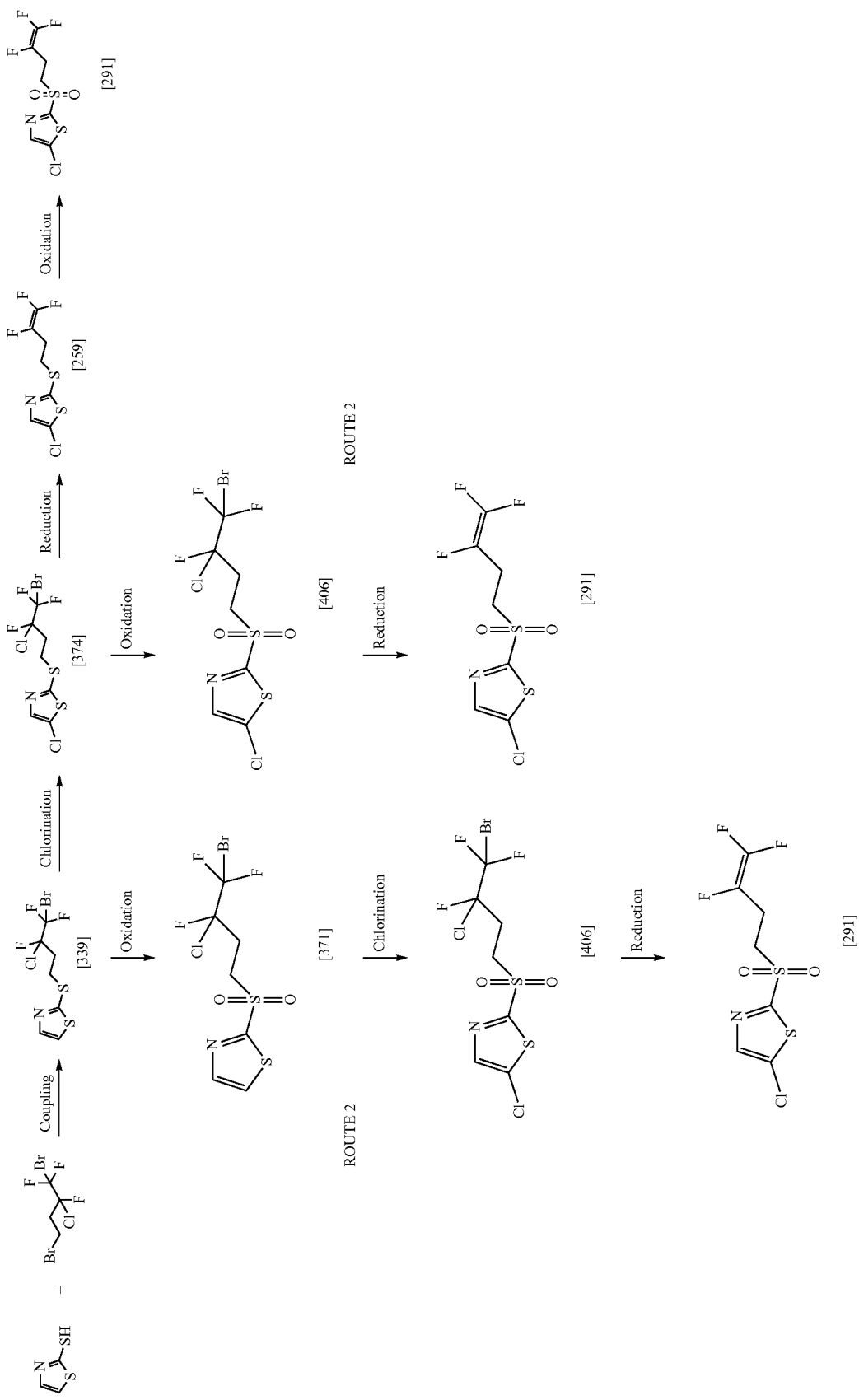

The synthetic pathway according to Route 1 is preferred; it is shown below, where the arrows 1, 2, 3 correspond to the alkylation (coupling), chlorination and dehalogenation (reduction) steps, respectively. The most preferred key intermediates, through which the synthesis of Route 1 passes, are named Intermediate A1, B1 and C1, respectively:

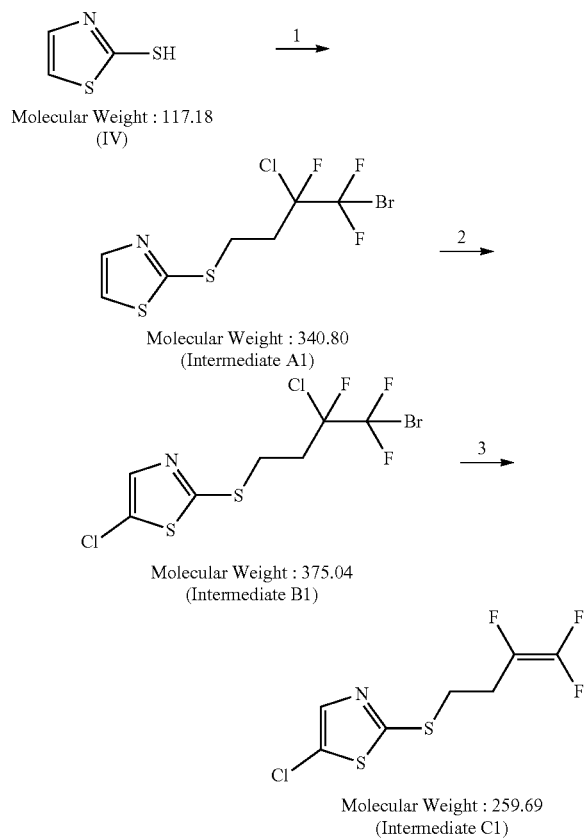

The efficiency of the process set forth above is further enhanced by telescoping steps, namely, by carrying a reaction mixture or worked-up solution from one step directly to the following step, without isolation of an intermediate product or exchange of solvent. In a multistep reaction it is often necessary to replace the solvent when advancing from one step to the next one. A series of tests reported below indicates that the synthetic pathway is amenable to telescopic design, starting with the synthesis of the 2-mercaptothiazole (IV), as described below, and moving on to the alkylation (1) and chlorination (2) using the same solvent. The solvent of choice meets two major requirements: (i) good solubilization capacity for 2-mercaptothiazole, say, not less than 10 wt %; and (ii) sufficient inertness to chlorination. Below are provided tests that can serve for solvent selection for use in a telescopic process. However, the process of the invention is not limited to a telescopic design; the process may be carried out with the isolation of one or more intermediates, their purification and exchange of solvents between the process steps. For example, synthesis of 2-mercaptothiazole (IV) and the alkylation step (1) can be telescoped, followed by solvent exchange before the chlorination step (2).

Accordingly, the invention is primarily directed to a process for preparing heterocyclic fluoroalkenyl sulfones and their thioether and sulfoxide precursors of the formula:

Cl—R—S(O)$_n$—(CH$_2$)$_2$—CF=CF$_2$    (Formula I')

wherein R is a heterocyclic, preferably five-membered, aromatic ring (especially thiazole), n is 0, 1 or 2, comprising a step of dehalogenation compound of the formula:

Cl—R—S(O)$_n$—(CH$_2$)$_2$—CFX$^1$—CF$_2$X$^2$    (Intermediate B)

wherein X$^1$ and X$^2$ are independently halogen atoms, to remove said X$^1$ and X$^2$ atoms.

In particular, the process comprises the steps of:
1) alkylating thiol R—SH, wherein R is a heterocyclic five-membered aromatic ring, in particular sulfur-containing ring selected from the group consisting of thiophene, thiazole and thiadiazole, most preferably thiazole, such that R—SH is a thiol of the formula:

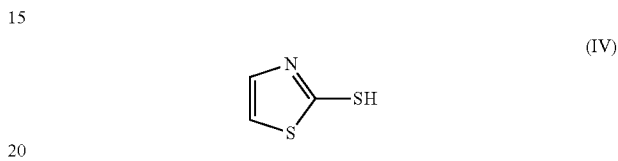

with a fluorinated haloalkane of the formula L-(CH$_2$)$_2$—CFX$^1$—CF$_2$X$^2$ in a first organic solvent, wherein L is a leaving group capable of displacement by a thiol group, for example, L is halide such as bromide or iodide; and X$^1$ and X$^2$ are halogen atoms which may be the same or different, e.g. chlorine, bromine or iodine, to form a thioether having the formula:

R—S—(CH$_2$)$_2$—CFX$^1$—CF$_2$X$^2$    (Intermediate A)

2) ring-chlorinating Intermediate A, optionally in a second organic solvent (namely, solventless reaction is possible), to produce chlorine-substituted compound of the formula:

Cl—R—S—(CH$_2$)$_2$—CFX$^1$—CF$_2$X$^2$    (Intermediate B)

and optionally oxidizing Intermediate B to its corresponding oxidized form Cl—R—S(O)$_n$—(CH$_2$)$_2$—CFX$^1$—CF$_2$X$^2$, wherein n is 1 or 2;

3) dehalogenation of Intermediate B or its oxidized form in a third organic solvent to remove said X$^1$ and X$^2$ atoms and produce a compound of the formula:

Cl—R—S(O)$_n$—(CH$_2$)$_2$—CF=CF$_2$    (n=0,1,2; Formula I')

and optionally oxidizing the compound of Formula I' in case that n=0 or n=1 to afford the heterocyclic fluoroalkenyl sulfone of the Formula I, possessing the nematicidal activity:

Cl—R—SO$_2$—(CH$_2$)$_2$—CF=CF$_2$    (Formula I)

It is noted that Formula I' encompasses the sulfones (n=2, specifically identified by Formula I) and their non-oxidized precursors. In particular, when n=0, a thioether fluorinated alkene compound is obtained following the dehalogenation, identified herein as Intermediate C:

Cl—R—S—(CH$_2$)$_2$—CF=CF$_2$    (Intermediate C)

It should also be noted that the solvents used in consecutive steps (e.g., the first and second solvents, used in the alkylation and chlorination) can be the same or different.

The preferred variant of the process comprises:
A) alkylating thiol R—SH to give the thioether R—S—(CH$_2$)$_2$—CFX$^1$—CF$_2$X$^2$    (Intermediate A);

B) ring-chlorinating Intermediate A to produce chlorine-substituted thioether compound of the formula:

Cl—R—S—(CH$_2$)$_2$—CFX$^1$—CF$_2$X$^2$    (Intermediate B)

C) dehalogenation of Intermediate B to remove the $X^1$ and $X^2$ halogen atoms and produce a thioether fluorinated alkene of the formula:

Cl—R—S—(CH$_2$)$_2$—CF=CF$_2$     (Intermediate C)

and optionally oxidizing Intermediate C to give the heterocyclic fluoroalkenyl sulfone (e.g., Fluensulfone):

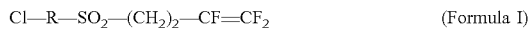

Cl—R—SO$_2$—(CH$_2$)$_2$—CF=CF$_2$     (Formula I)

Preferably, R is thiazole, $X^1$ is Cl and $X^2$ is Br. Hence Intermediates A1 and B1 represented by the following formulas, respectively:

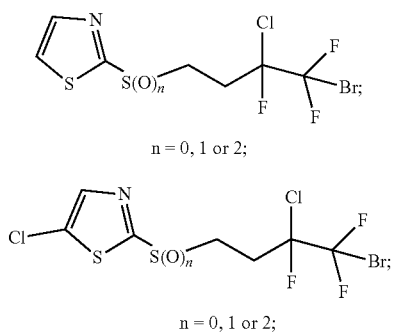

form additional aspects of the invention; especially useful are Intermediates A1 and B1 where n=0, and salts thereof (acid addition salts):

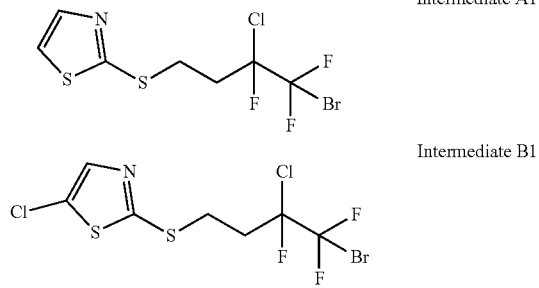

The starting materials that are needed for the alkylation step (1) are commercially available or can be prepared by known procedures.

The starting material L-(CH$_2$)$_2$—CFX$^1$—CF$_2$X$^2$ where the leaving group L is halide (Hal) is named herein "fluorinated haloalkyl halide"; when $X^1$ and $X^2$ are different from one another, the starting material is named "mixed fluorinated haloalkyl halide", such as 1,4-dibromo-2-chloro-1,1,2-trifluorobutane (Hal is Br, $X^1$ is Cl and $X^2$ is Br). These compounds can be prepared, for example, by the addition of halogen (Cl$_2$, Br$_2$) or mixed halogen (BrCl, ICl, IBr) to the double bond of 4-halo-1,1,2-trifluorobutene of the formula Hal-(CH$_2$)$_2$—CF=CF$_2$ in dichloromethane, to afford the vicinal dihalide of the formula Hal-(CH$_2$)$_2$—CFX$^1$—CF$_2$X$^2$, e.g., chlorine/bromine/iodine atoms on the adjacent carbons, or by other techniques that can be found in the literature, e.g., in a paper by Shellhamer et al. [Journal of Organic Chemistry 73 (12) p. 4532-4538 (2008) and supporting information]. Another useful technique consists of reacting ethylene with CF$_2$X$^1$—CFX$^2$X$^3$, as described by Tarrant et al. [The Journal of Organic Chemistry 34(4), p. 864-869 (1969)].

The other starting material that participates in the alkylation step, the thiol (IV), namely, 2-mercaptothiazole, can be obtained by a cyclization reaction as shown in U.S. Pat. Nos. 2,603,647 and 2,603,648, that is, reacting thiocyano acetaldehyde with hydrogen sulfide or with thiourea.

A preferred approach to the synthesis of the thiol (IV) that fits well into the contemplated telescopic design, and hence forms another aspect of the invention, includes the step of recovering a worked-up solution from the synthesis of thiol (IV), wherein the thiol (IV) is dissolved in a water-immiscible organic solvent, such that the worked-up solution can be carried to the alkylation step without isolation of the thiol(IV).

This approach can be realized with the preparation method shown below and described in U.S. Pat. No. 5,994,553, which involves a ring closure reaction of chloroacetaldehyde (2-CAA) with a dithiocarbamate salt (abbreviated DTC) to give 4-hydroxy-2-thiazolidinethione (135 in the reaction scheme depicted below, or an isomer thereof where the hydroxy is attached to the carbon at position 5 of the ring, or a tautomer thereof; hereinafter collectively indicated by the name 4-hydroxy-2-thiazolidinethione), followed by dehydration to lose a water molecule and arrive at 2-mercaptothiazole (abbreviated MTZ):

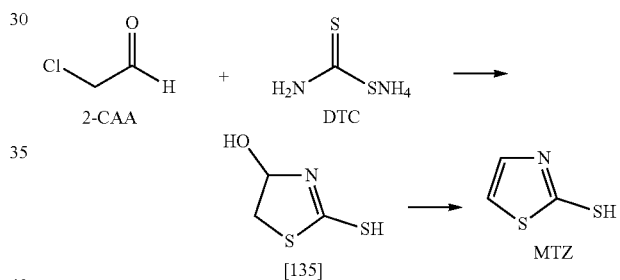

Thus, 2-mercaptothiazole is obtained by a ring closure reaction of chloroacetaldehyde with a dithiocarbamate salt, that takes place in an acidic aqueous medium, generally at room temperature, to form 4-hydroxy-2-thiazolidinethione, an isomer thereof or a mixture of isomers, followed by a dehydration reaction that is performed at elevated temperature, wherein 4-hydroxy-2-thiazolidinethione undergoes dehydration in the aqueous medium, followed by extraction of the so-formed 2-mercaptothiazole with water-immiscible organic solvent, whereby a worked-up organic solution consisting of the 2-mercaptothiazole dissolved in the water-immiscible organic solvent is recovered.

Preferably, 2-mercaptothiazole is obtained by reacting chloroacetaldehyde with a dithiocarbamate salt [$_2$HNC(S)S$^-$M$^+$, wherein M$^+$ is preferably ammonium; the ammonium salt is abbreviated herein ADTC; but sodium and potassium salts can also be used] in an acidic aqueous environment (the acidic environment is supplied by inorganic or organic acid) to form an aqueous suspension of 4-hydroxy-2-thiazolidinethione, heating the reaction mixture, allowing the reaction to reach completion, extracting the reaction mixture with water-immiscible organic solvent, separating the reaction mass into organic and aqueous phases, and either isolating (and optionally purifying) 2-mercaptothiazole from the organic phase, or carrying the 2-mercaptothiazole-containing worked-up organic solution to the alkylation step.

For example, an aqueous chloroacetaldehyde solution is acidified by the addition of a mineral acid such as hydrochloric acid or organic acid, following which an aqueous solution of the dithiocarbamate salt is gradually fed to the reaction vessel. The addition of the salt is carried out over a period of time, say, up to several hours; the addition is carried out at a temperature from 0 to 50° C., e.g., from 20-35° C.

Upon addition of ADTC, 4-hydroxy-2-thiazolidinethione precipitates from the aqueous solution and a suspension is formed. After the ADTC addition has been completed, the suspension is kept under stirring for an additional period time.

To convert 4-hydroxy-2-thiazolidinethione into 2-mercaptothiazole, the reaction mixture is heated to a temperature in the range from 35° C. to the reflux temperature, e.g., from 50 to 90° C.

Next, the work-up of the reaction mixture includes extraction of 2-mercaptothiazole. The choice of the organic solvent for the extraction of 2-mercaptothiazole determines whether the process would fit into a telescopic design. That is, one may choose a solvent that is well-suited for the 2-mercaptothiazole workup step and the successive chlorination step. The factors influencing the choice of solvent are water-immiscibility, high solubilization capacity for 2-mercaptothiazole and sufficiently inertness to chlorination reagents, as now described in detail.

The primary requirement placed on the organic solvent is that it exhibits poor solubility in water. By 'water immiscible organic solvent' is meant a solvent with solubility in water at room temperature of less than 5.0 g/100 ml, preferably less than 3.0 g/100 ml, more preferably less than 1.0 g/100 ml, and even more preferably less than 0.1 g/100 ml. Especially preferred are solvents with solubility of less than 0.05 g/100 ml. A variety of organic solvents may be considered for the extraction of 2-mercaptothiazole, such as alkyl-substituted benzene (e.g., toluene), halogenated aliphatic hydrocarbons (e.g., 1,2-dichloroethane), aliphatic nitriles (e.g. n-butyronitrile, abbreviated NBN and iso-butyronitrile, abbreviated IBN), ethers of the formula R1-O—R2, wherein R1 is aliphatic ring and R2 is straight or branched alkyl (such as cyclopentyl methyl ether, abbreviated CPME), higher alcohols with not less than four carbon atoms in the molecule (e.g., isobutyl alcohol and n-pentanol) and esters such as $CH_3$—COO—R3 wherein R3 is straight or branched alkyl with not less than three carbon atoms (e.g., isopropyl acetate, abbreviated IPAc).

However, 2-mercaptothiazole exhibits fairly low solubility in some of the aforementioned solvents; the reduced solubility may lead to the formation of an insoluble phase with the consequence that the resulting reaction mass does not lend itself to easy workup e.g., phase separation may be difficult to achieve (e.g., may require addition of extra solvent etc. and additional efforts). Still, there are suitable classes of solvents offering adequate level of 2-mercaptothiazole solubilization, specifically aliphatic nitriles (e.g. NBN and IBN), ethers R1-O—R2 (e.g., CPME), higher alcohols (e.g., possessing not less than four carbon atoms in the molecule, such as isobutyl alcohol and 1-pentanol) and esters $CH_3$—COO—R3 (e.g. IPAc).

As pointed out above, once the 2-mercaptothiazole formation reaction and workup are completed, a worked-up organic solution is collected. 2-mercaptothiazole can be isolated from the organic phase by conventional techniques, such as precipitation/crystallization and purified by recrystallization or chromatographic purification. The isolated 2-mercaptothiazole then undergoes the alkylation reaction.

However, if the organic solvent used for the 2-mercaptothiazole formation reaction is sufficiently inert towards chlorination, then the 2-mercaptothiazole-containing worked-up solution may be carried directly to the next step (the alkylation step) and subsequently to the chlorination step.

To summarize, the preferred water-immiscible solvent for use in the process, starting from 2-mercaptothiazole workup and advancing to the chlorination reaction, meets the following two requirements:

1) the solubility of 2-mercaptothiazole in the first solvent at 25° C. is not less than 5 wt %, preferably not less than 10 wt %, more preferably not less than 15 wt %, e.g., from 15 to 25 wt %; and
2) the solvent is sufficiently inert to at least one chlorinating agent that chlorinates aromatic rings (for example, $Cl_2$, sulfuryl chloride, N-chlorosuccinimide and trichlorocyanuric acid).

There are different techniques by which a solvent can be tested to determine its stability against chlorination in the context of the present invention. For example, when the solvent is treated with a chlorination reagent under conditions required to achieve acceptable level of aromatic chlorination (e.g., temperature, time, catalyst and light irradiation), the amount of chlorinated derivates of the said solvent that is formed does not exceed 5% (preferably <3%, more preferably <1%)), relative to the initial amount of the solvent, as measured by appropriate method.

Tests are provided below to illustrate if a solvent is sufficiently inert to sulfuryl chloride (e.g., upon stirring 8 ml solvent with 2 ml $SO_2Cl_2$ for five hours at 40° C., the level of chlorinated derivates of said solvent measured by GC analysis is less than 5 Area %; and to chlorine gas (e.g., upon bubbling chlorine at a rate of 1 mL/min for 2 hours through 20 ml solvent, followed by closing the reaction vessel and stirring the sample for eight hours at room temperature, the level of chlorinated derivatives of said solvent measured by GC analysis is less than 5 Area %.

NBN, IBN and CPME emerged from the experimental work reported below as suitable solvents for the telescopic process.

Turning now to the alkylation step (1), the alkylation reaction comprises combining the thiol R—SH, e.g., 2-mercaptothiazole with a fluorinated haloalkyl halide Hal-$(CH_2)_2$—$CFX^1$—$CF_2X^2$ in an organic solvent in the presence of a base under heating, e.g., from 0° C. to reflux temperature, allowing the reaction to reach completion, collecting a worked-up organic solution and either isolating (and optionally purifying) Intermediate A from the worked-up organic solution, or carrying the Intermediate A-containing organic solution to the chlorination step.

For example, a reaction vessel is charged with a solvent selected from the group of solvents mentioned above (e.g. ethers, aliphatic and aromatic hydrocarbons, chlorinated solvents, esters and ketones; e.g., tetrahydrofuran, toluene, chlorobenzene) and the purified thiol. Alternatively, when a telescopic design is intended, the crude thiol-containing worked-up solution (e.g., 2-mercpatothiazole-containing NBN solution or 2-mercpatothiazole-containing CPME solution) is directly added to the alkylation reactor.

The molar ratio 2-mercpatothiazole:base is preferably from 0.01 to 10. Suitable bases include alkali carbonates, e.g., $Na_2CO_3$ and $K_2CO_3$, and alkali hydroxide. The base may be added in a solid form, e.g., granules/pellets, or in the form of an aqueous solution, e.g., with the concentration of alkali carbonate in the solution fed to the reaction mixture being from 0.01M up to saturation. Hence the reaction mixture may consist of a single organic phase with the added solid base, or a liquid-liquid biphasic system consisting of a liquid organic phase and a liquid aqueous phase where the alkaline agent is dissolved. In both cases the reaction may benefit from the addition of phase transfer catalyst such as tetrabutylammonium bromide (TBAB); the loading of the phase transfer catalyst is generally about 0.1 to 10 molar % relative to 2-mercpatothiazole.

Next, the fluorinated haloalkyl halide Hal-$(CH_2)_2$—$CFX^1$—$CF_2X^2$, especially a mixed fluorinated haloalkyl halide such as 1,4-dibromo-2-chloro-1,1,2-trifluorobutane, is added to the preferably heated, vigorously stirred reaction mixture. It should be noted that the molar ratio 2-mercpatothiazole:Hal-$(CH_2)_2$—$CFX^1$—$CF_2X^2$ may vary broadly, e.g., from 1:10 to 10:1 excess of 1,4-dibromo-2-chloro-1,1,2-trifluorobutane is readily recoverable by distillation. Excess of MTZ may be recovered by precipitation/crystallization.

After the Hal-$(CH_2)_2$—$CFX^1$—$CF_2X^2$ addition has been completed, the reaction mixture is kept under stirring for an additional period time. The workup includes addition of water, acidification and phase separation to collect the worked-up organic solution with Intermediate A dissolved therein. Crude Intermediate A can be isolated from the worked-up organic solution, e.g., by concentration, and purified (e.g., by distillation or chromatographic cleaning). Alternatively, the worked-up solution is directed to the chlorination step.

Turning now to the chlorination step (2), the chlorination reaction comprises combining Intermediate A and a chlorinating agent, preferably in an organic solvent (for example, by adding a chlorinating agent to a reaction vessel that was previously charged with Intermediate A and the organic solvent) completing the reaction and recovering Intermediate B from the reaction mixture.

Chlorinating agents known to be effective in aromatic chlorination, such as $Cl_2$, sulfuryl chloride, N-chlorosuccinimide and trichlorocyanuric acid, to name a few major halogenating agents, can be used. Any organic solvent that is sufficiently inert to the chlorinating agent under consideration may be used; such solvents include carbon tetrachloride, chloroform, chlorobenzene, 1,2-dichlorobenzene, 1,3-dichlorobenzene, acetonitrile and dimethylformamide. Preferably, however, the worked-up solution recovered in the alkylation step is dried (e.g., distillation is performed to reach 0.1 w/w % water content), and the dried solution charged to the chlorination reactor, e.g., a solution of Intermediate A1 in NBN. Then the chlorinating agent is gradually fed to the reactor.

For example, chlorination of Intermediate A1 to form Intermediate B1 is achieved with the aid of sulfuryl chloride:

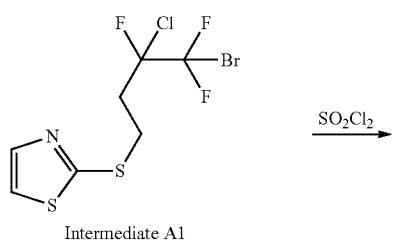

Intermediate A1

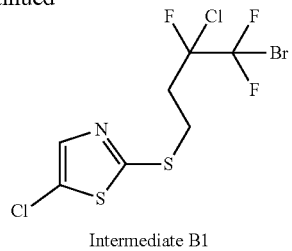

Intermediate B1

Sulfuryl chloride is fed to the reaction mixture either in a neat form, or in the form of a solution in the same organic solvent that is used to dissolve Intermediate A, e.g., NBN. The addition of the $SO_2Cl_2$ solution may be carried out gradually, over a period of time, for example, up to several hours. The chlorination reaction is exothermic.

Upon completion of $SO_2Cl_2$ addition, the reaction mixture is stirred at ambient temperature for additional period of time, during which period the reaction mass is periodically sampled to monitor reaction progress by a suitable analytical method.

The workup includes addition of water, filtration and separation the filtrate into organic and aqueous phases. Intermediate B1 is separated from the organic phase by removal of volatiles, and is optionally purified by fractional distillation or chromatographic cleaning before it moves on the next (dehalogenation) step.

In another embodiment of the invention, chlorination of Intermediate A1 to form Intermediate B1 is achieved with the aid of elemental chlorine:

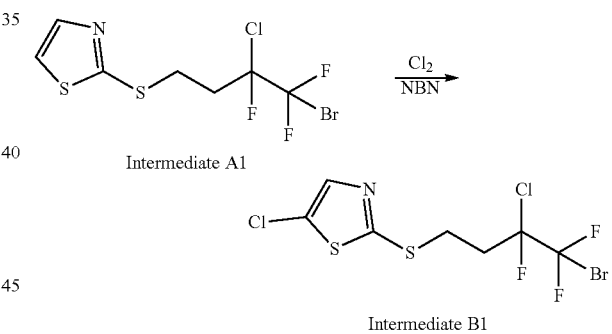

Chlorine is fed to a reaction vessel that was previously charged with Intermediate A1, an organic solvent (e.g., the worked-up organic solution recovered in the alkylation step; the worked-up organic solution is dried before the chlorination step) and an organic base such as triethylamine. The amount of chlorine that is bubbled through the solution and available to react with Intermediate A1 is preferably about 1.0 to 2.5 equivalents. The total amount of chlorine that needs to be supplied to the reaction to achieve acceptable yield may depend on the reaction temperature (the reaction is exothermic, cooling the reaction mixture and keeping it at room temperature may require increased amounts of chlorine).

The workup includes washing with water and separation into organic and aqueous phases. Intermediate B1 is separated from the organic phase by removal of volatiles and is optionally purified by fractional distillation or chromatographic purification before it moves on the next (dehalogenation) step.

As pointed out above, there is an alternative to telescoping the steps of 2-mercaptothiazole synthesis, alkylation (1) and chlorination (2). The alternative consists of carrying the 2-mercaptothiazole-containing worked-up solution (for example, in C4-C5 water-immiscible alkanol such as 1-pentanol) to the alkylation step, with isolation of the alkylation product (Intermediate A1) and solvent exchange prior to the chlorination reaction, e.g., to halogenated aromatic hydrocarbon such as chlorobenzene or another solvent selected from the list of chlorination solvents mentioned above.

Turning now the dehalogenation step (3), elimination of the two halogen atoms $X^1$ and $X^2$ on the adjacent carbons at positions 1 and 2 of Intermediate B [Cl—R—S—$(CH_2)_2$—$CFX^1$—$CF_2X^2$], such as Intermediate B1:

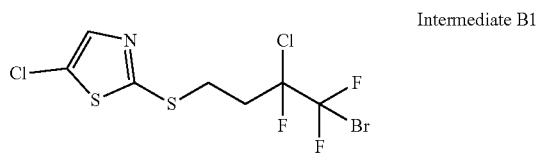 [SMILES: FC(F)(Br)C(F)(Cl)CCSc1ncc(Cl)s1]

Intermediate B1 is preferably achieved using a reducing agent, e.g., strong reducing metal, in particular zinc. The metal works well in combination with a suitable solvent, e.g., a lower alcohol such methanol or ethanol, or acetic acid, typically at elevated temperature. The Zn/methanol combination is preferred; the reaction by-product is(are) the corresponding zinc halide salt(s). The Zn/methanol combination, which is known to serve for dehalogenation of simple vicinal dihalide, was also found to be effective for selective dehalogenation of the thioether bearing the halogenated-fluorinated alkane chain (Intermediate B1) to arrive at the corresponding thioether fluorinated alkene (Intermediate C1).

The preferred dehalogenation reaction is shown below:

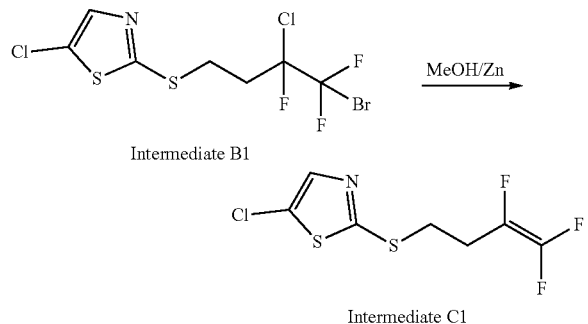

The dehalogenation reaction is carried out by charging a reactor with methanol and zinc metal (preferably in a granular or a powder form, but other metal forms such as wire, sheet and wool can also be used), and adding Intermediate B (e.g., B1) to the reaction mixture.

The weight ratio zinc:methanol may vary within a broad range. If needed, the metal may be activated prior to the introduction of Intermediate B, by known methods, e.g. with the aid of a small amount of elemental bromine or addition of zinc halide. The addition of Intermediate B preferably begins after the (optionally activated) zinc-containing medium is heated to an elevated temperature, but the reaction also advances at ambient temperature, albeit at a slower rate.

After the addition of Intermediate B has been completed, the reaction mixture is kept under stirring for an additional period time, at elevated temperature. The reaction product, Intermediate C, specifically Intermediate C1 {5-chloro-2-(3,4,4-trifluoro-3-buten-1-yl)thio]thiazole}, is separated by conventional techniques (cooling, acidification, and recovery of the organic phase) and purified by fractional distillation or chromatography.

Lastly, Compound C1 {5-chloro-2-(3,4,4-trifluoro-3-buten-1-yl)thio]thiazole} can undergo oxidation to give Fluensulfone. The oxidation reaction is accomplished by methods known in the art, using oxidizing agents such as hydrogen peroxide, m-chloroperoxybenzoic acid, peroxyacetic acid, peroxy-benzoic acid, magnesium monoperoxyphthalate, potassium peroxy monosulfate, as shown in EP 1200418 and US 2006/0004196. The oxidizing agents can also be used to accomplish other oxidation reactions mentioned herein, to convert sulfide to sulfone, namely, Intermediate B to its oxidized form:

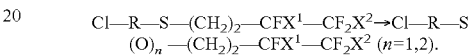

The nematicidialy active material, e.g., Fluensulfone, can be used for purposes described in EP 1200418.

Turning now to Route 2, it is seen in the general scheme above that the process diverts to Route 2 following the chlorination step, where the synthetic pathway proceeds to the oxidation of intermediate B, to give the corresponding sulfone form of Intermediate B, which undergoes dehalogenation to produce the active compound, namely Fluensulfone. Route 2 is therefore described by a process comprising the following steps:

A) alkylating thiol R—SH to give the thioether

 (Intermediate A);

B) ring-chlorinating Intermediate A to produce chlorine-substituted thioether compound of the formula:

 (Intermediate B)

C) oxidizing Intermediate B to produce the corresponding sulfone of the formula:

 (Intermediate B, sulfone form)

D) dehalogenation of the sulfone form of Intermediate B to give the heterocyclic fluoroalkenyl sulfone (i.e., the nematicidialy active material):

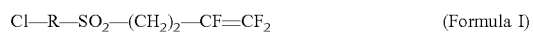 (Formula I)

The preferred synthetic pathway according to Route 2 is shown below, passing through Intermediate A1, B1 and B2, where the arrows 1, 2, 3 correspond to the alkylation (coupling), chlorination and oxidation steps, respectively:

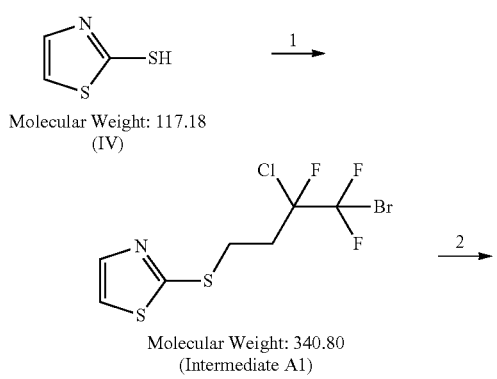

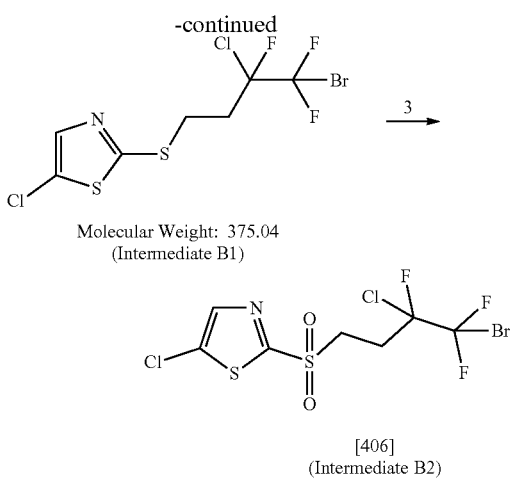

Molecular Weight: 375.04
(Intermediate B1)

[406]
(Intermediate B2)

Because Routes 1 and 2 share the steps of alkylation (1) and chlorination (2), the description that follows pertains to the oxidation reaction (3) and the subsequent dehalogenation to give the active compound.

The oxidation reagent is selected from the list set out above, e.g., of powerful oxidizers capable of achieving good yields in converting sulfide to the corresponding sulfone. For example, a mixture consisting of 1 mole of potassium peroxymonosulfate with 0.5 mole of potassium bisulfate and 0.5 mole of potassium sulfate ($KHSO_5 \cdot 0.5KHSO_4 \cdot 0.5K_2SO_4$ commercially available as Oxone®) can be used. The salt mixture is not soluble in organic solvents, but is capable of advancing oxidation reactions in aqueous/organic solvent systems such as alkanol-water (e.g., methanol-water or ethanol-water) or acetic acid-water, preferably at low temperatures to prevent the loss of active oxygen, e.g., temperatures up to 25° C., and even below 10° C. can be utilized, optionally in the slightly alkaline pH range. On completion of the oxidation reaction, filtration of the insoluble salt and removal the alcohol solvent, the product is recovered by extractive work-up of the aqueous phase.

Accordingly, a preferred variant of the oxidation reaction comprises progressively adding an aqueous solution of the reagent $KHSO_5 \cdot 0.5KHSO_4 \cdot 0.5K_2SO_4$ to a reaction vessel that was previously charged with alkanol (e.g., methanol) and the intermediate B1 {namely, 2-[(4-bromo-3-chloro-3,4,4-trifluorobutyl)thio]-5-chloro-1,3-thiazole}.

The total amount of the reagent $KHSO_5 \cdot 0.5KHSO_4 \cdot 0.5K_2SO_4$ is divided into several portions which are supplied to the reaction at two consecutive stages (corresponding to —SO— → —SO$_2$—), wherein each stage includes addition of a major portion (say, about 1.0-1.1 equivalents of the reagent) in the form of an aqueous solution at a temperature below 10° C. and addition of an auxiliary portion (say, less than 0.1 equivalents of the reagent) at a temperature above 10° C., e.g., around room temperature, under stirring. The second stage is run under pH control, wherein the pH of the reaction mixture is kept slightly alkaline the with the aid of a base such as alkali hydroxide.

For example, the process comprises the following steps:
gradually adding a first major amount the reagent in an aqueous form (e.g., 1.0-1.1 equivalents) to the reaction mixture at a temperature of 2-8° C., e.g., around 5° C.;
maintaining the suspension under stirring at a temperature of 17-23° C., e.g., around 20° C.;
adding a first auxiliary amount, say, less than 0.1 equivalents, to the suspension;
maintaining the suspension under stirring;
cooling the suspension to a temperature of 2-8° C., e.g., around 5° C.;
adjusting the pH of the reaction mixture at a slightly alkaline range, e.g., from 8 to 9;
gradually adding a second major amount of the reagent in an aqueous form (e.g., 1.0-1.1 equivalents);
maintaining the suspension under stirring at a temperature of 17-23° C., e.g., around 20° C., at said pH range;
adding a second auxiliary amount, say, less than 0.1 equivalents, to the suspension;
and maintaining the suspension under stirring to complete the oxidation reaction.

The reaction mixture is worked-up by separating the insoluble salt, e.g., by filtration, optionally treating the liquid phase with a reducing agent to eliminate residual oxidant, removing the alkanol component of the liquid phase, e.g., by distillation, and recovering the oxidation product B2 from the aqueous phase, e.g., by extraction with a suitable organic solvent, following which the oxidation product B2 is collected from the extractant, e.g., by evaporating the extractant, in the form of a white solid.

The resultant intermediate B2, which is chemically named 2-(4-bromo-3-chloro-3,4,4-trifluorobutylsulfonyl)-5-chloro-1,3-thiazole:

Intermediate B2

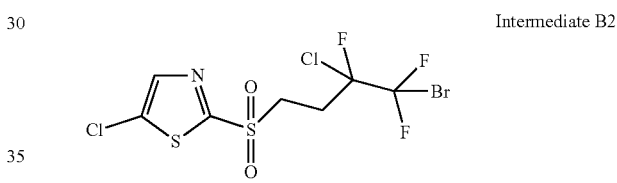

forms another aspect of the invention.

Next, the Intermediate B2 undergoes dehalogenation to give the nematicidialy active compound, e.g., Fluensulfone. The conditions are similar with those applied in the dehalogenation step described above for Route 1. The reductant of choice is zinc (e.g., in powder or granular form); but this time the dehalogenation reaction preferably takes place in ether such as tetrahydrofuran under heating, e.g., in refluxing THF after an in-situ activation of zinc by known methods, e.g., chemical activation with the aid of additives and promoters can be achieved by addition of a small amount of elemental halogen (crystals of iodine or liquid bromine), addition of zinc halide, cuprous or cupric salts, e.g., cupric bromide. Other solvents that can be used in the dehalogenation step are DMF and methanol.

The addition of Intermediate B2 preferably begins after the (optionally activated) zinc-containing medium is heated to an elevated temperature, but the reaction also advances at ambient temperature, albeit at a slower rate. The progress of the reaction is tracked (e.g., liquid chromatography-mass spectrometry analysis) to determine the conversion of Intermediate B2. If needed, a supplementary amount of the additives and promoters mentioned above is introduced into the reaction mixture. The reaction is then allowed to reach completion, e.g., under refluxing and stirring for several hours.

Work-up to recover the active compound includes filtration of unreacted metal, acidification, extractive procedures and purification e.g., by column chromatography methods and other

Abbreviations

Compounds are interchangeably identified herein by their molecular weights and the following abbreviations; when a tautomer exists, it is also encompassed by the structures and names used herein:

2-CAA: chloroacetaldehyde
ADTC: dithiocarbamate ammonium salt
135: 4-hydroxy-2-thiazolidinethione
MTZ, 117: 2-mercaptothiazole
1,4-DiBr: 1,4-dibromo-2-chloro-1,1,2-trifluorobutane
339: 2-[(4-bromo-3-chloro-3,4,4-trifluorobutyl)thio]thiazole
374: interchangeably named herein 5-chloro-2-[(4-bromo-3-chloro-3,4,4-trifluorobutyl)thio]thiazol; and 2-[(4-bromo-3-chloro-3,4,4-trifluorobutyl)thio]-5-chloro-1,3-thiazole
259: 5-chloro-2-[(3,4,4-trifluoro-3-buten-1-yl)thio]thiazole
406: 2-(4-bromo-3-chloro-3,4,4-trifluorobutylsulfonyl)-5-chloro-1,3-thiazole

EXAMPLES

Analytical Methods

1) LC-MS Analysis

The LC-MS analyses were performed using a Thermo Scientific LC/MS system consisting of an Accela 600 pump with degasser, Accela PDA detector, Accela autosampler, and an Exacitve MS Detector (Orbitrap). A Hypersil Gold Column (250×4.6 mm, LOT 7327, #0160665T) was used for the measurement and the temperature of the column oven was set to 40° C. The following program was used: 0-2 min: 50:50 mixture of MeCN (acetonitrile) and Formic acid (+0.1 M formic acid solution in water). 2-8 min: a 60:40 ratio of MeCN to formic acid was chosen. 8-15 min a 95:5 ratio of MeCN to formic acid was used. From 15-18 min a 30:70 ratio of MeCN to formic acid was used. At each time interval the flow is set to 1000 μl/min. An overall runtime of 15 was recorded and a wavelength in a range of 230-360 nm was measured, with the A channel set to 254 nm.

2) GC-MS Analysis

The GC-MS analyses were performed using a Thermo Scientific GC/MS model ITQ1100 equipped with a Restek Rxi-5Sil MS column. The following oven temperature program was used: initial temperature=34° C., initial time 2 min, heating with 40° C./min to 125° C., and then with no holding time heating with 10° C./min to the final temperature of 330° C. This final temperature was then held for 5 min, after which the end of the temperature program was reached.

Preparation 1

Preparation of 2-mercaptothiazole (Compound IV)

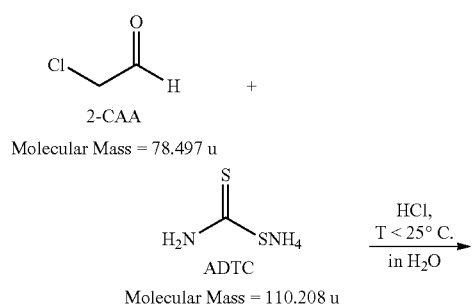

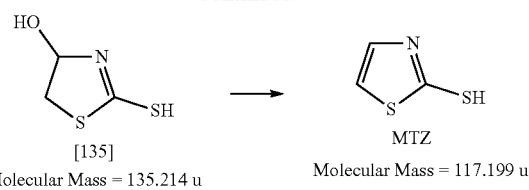

2-mercapthothizaole was prepared according to the procedure described in U.S. Pat. No. 5,994,553. When the reaction was complete, using an overall amount of 50.0 g 2-Chloroacetaldehyde, the reaction mixture was cooled to 20° C. and extracted once with 400 g NBN and twice with 100 g NBN.

The organic extracts were combined together. MTZ is obtained in NBN solution in a yield of around 75-80% by quantitative analysis of the solution vs. analytical standard.

Preparation 2

Preparation of 2-mercaptothiazole (Compound IV)

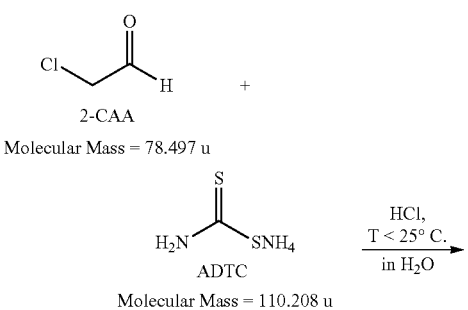

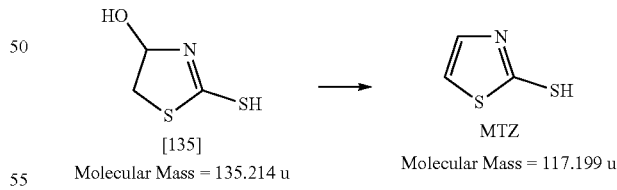

2-mercapthothizaole was prepared according to the procedure described in U.S. Pat. No. 5,994,553. When the reaction was complete, using an overall amount of 110 g 2-chloroacetaldehyde, 1-pentanol is added (200 gr) and temperature is increased to 70° C. The reaction is stirred for 1.5 hours until completion.

The mixture is cooled to 20° C. and filtered followed by phase separation. The water phase is extracted with pentanol twice (2×50 gr) to obtain a solution MTZ in pentanol.

Example 1 (Route 1)

Preparation of Intermediate A1 by Alkylation of Compound IV 2-[(4-bromo-3-chloro-3,4,4-trifluorobutyl)thio]thiazole

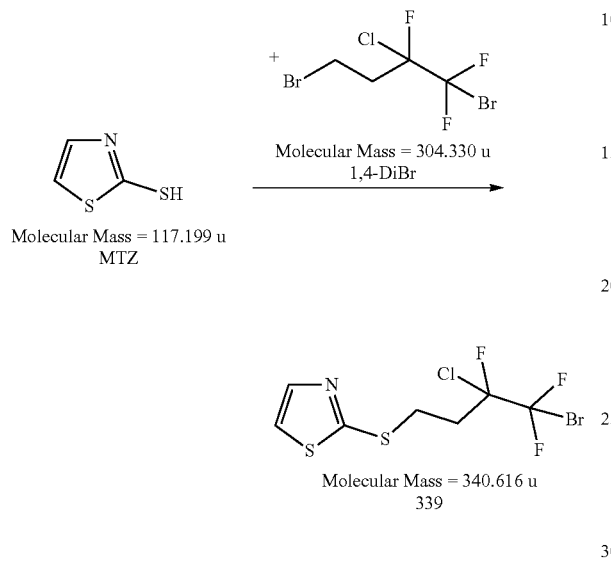

Example 2 (Route 1)

Preparation of Intermediate B1 by chlorination of Intermediate A1 using $SO_2Cl_2$ 5-chloro-2-[(4-bromo-3-chloro-3,4,4-trifluorobutyl)thio]thiazole

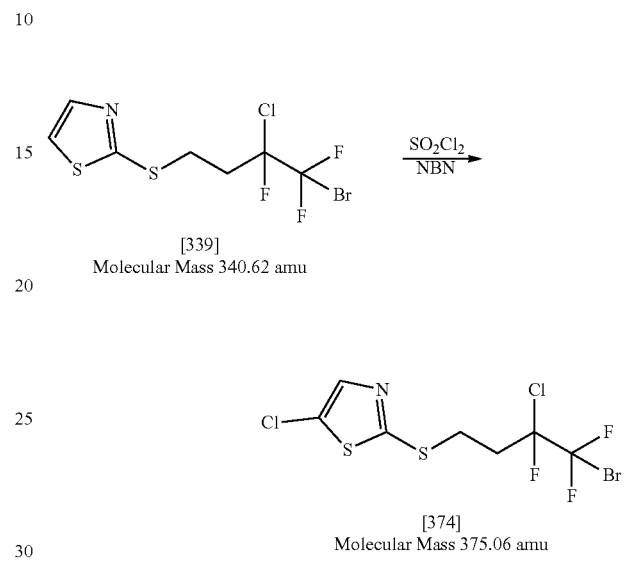

Into 1 L reactor equipped with a stirrer, reflux condenser, thermometer and pH meter was added the MTZ solution in NBN as obtained in Preparation 1 (350 g of 16.5 wt % MTZ solution, 492.79 mmol, 1.0 equivalent) and water (25 g), followed by dropwise addition under stirring of aqueous sodium hydroxide (15 wt %) to reach pH 4.

Next, TBAB (7.54 g, 23.41 mmol) is added to the reaction mixture, followed by the addition of 1,4-DiBr (143.5 g, 468.12 mmol, 0.95 equivalent). Then $Na_2CO_3$ was added slowly (11.53 g, 122.7 mmol, 0.23 equivalents). The reaction mixture was then heated to 70° C. and aqueous sodium hydroxide solution (about 100 g of 15 wt % solution) was added to reach pH ~8-8.2. The reaction mixture was kept under stirring for approximately one hour, during which period the reaction mixture was periodically sampled to track the progress of the reaction.

The reaction mixture was cooled to room temperature. pH was corrected to 4 with the aid of aqueous HCl solution (32 wt). The reaction mixture was filtered. The filtrate was separated into aqueous and organic phases. The organic phase (440 g) consists of ~35 wt % of the entitled product (Intermediate A1) dissolved in NBN. Yield: ~95% by quantitative analysis vs. analytical standard. The solution was used without further purification in the chlorination reaction.

The identity of Intermediate A1 was confirmed by GC-MS-analysis as outlined above. Therefore, a purified sample (purified by column separation) was injected resulting in one single peak at a retention time of 10.56 min. The MS spectrum of this peak shows the expected splitting pattern of the mass peak around m/z 340.6.

Figure 1B:
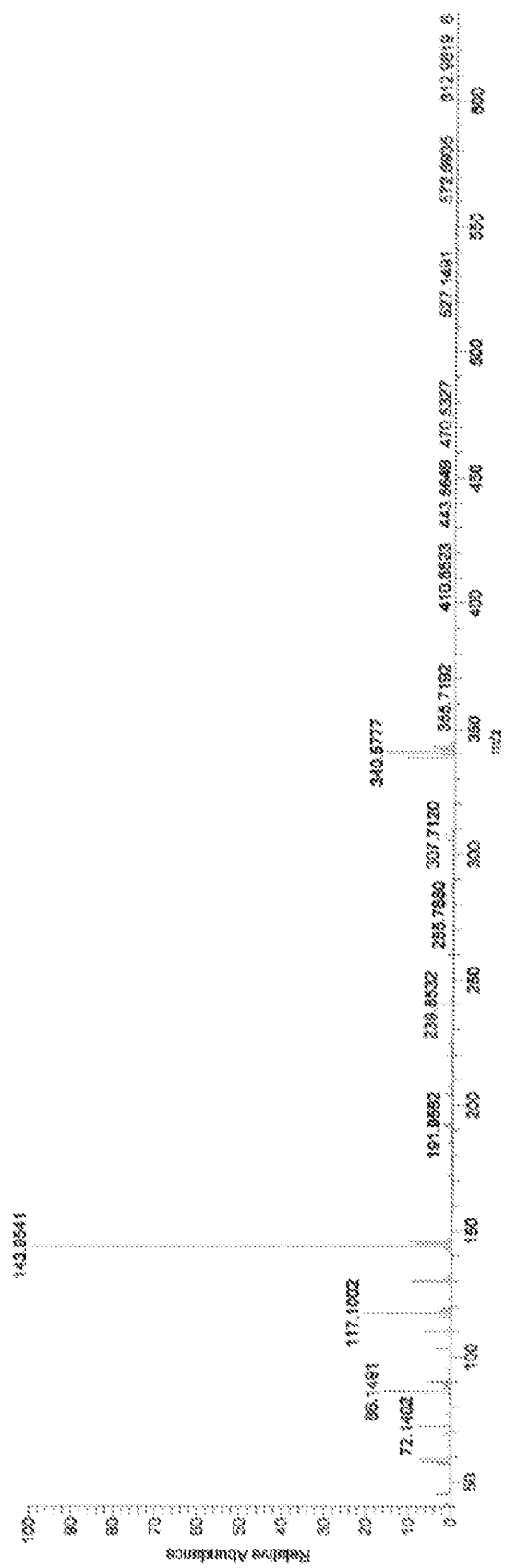
Figure 2A:
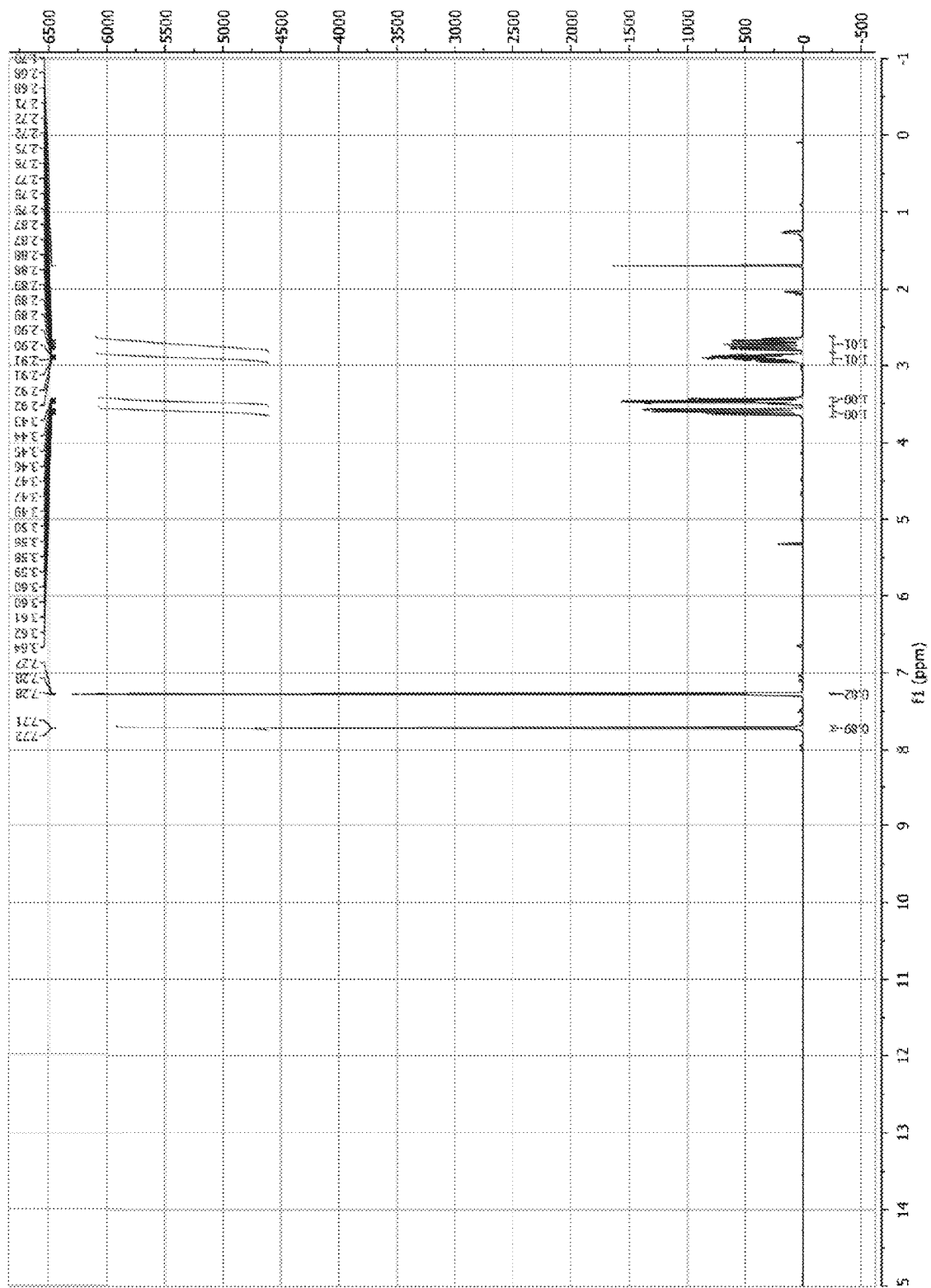
FIGS. 2A, 2B and 2C show 1HNMR, 13CNMR and 19FNMR spectra, respectively, according to an example.
Figure 2B:
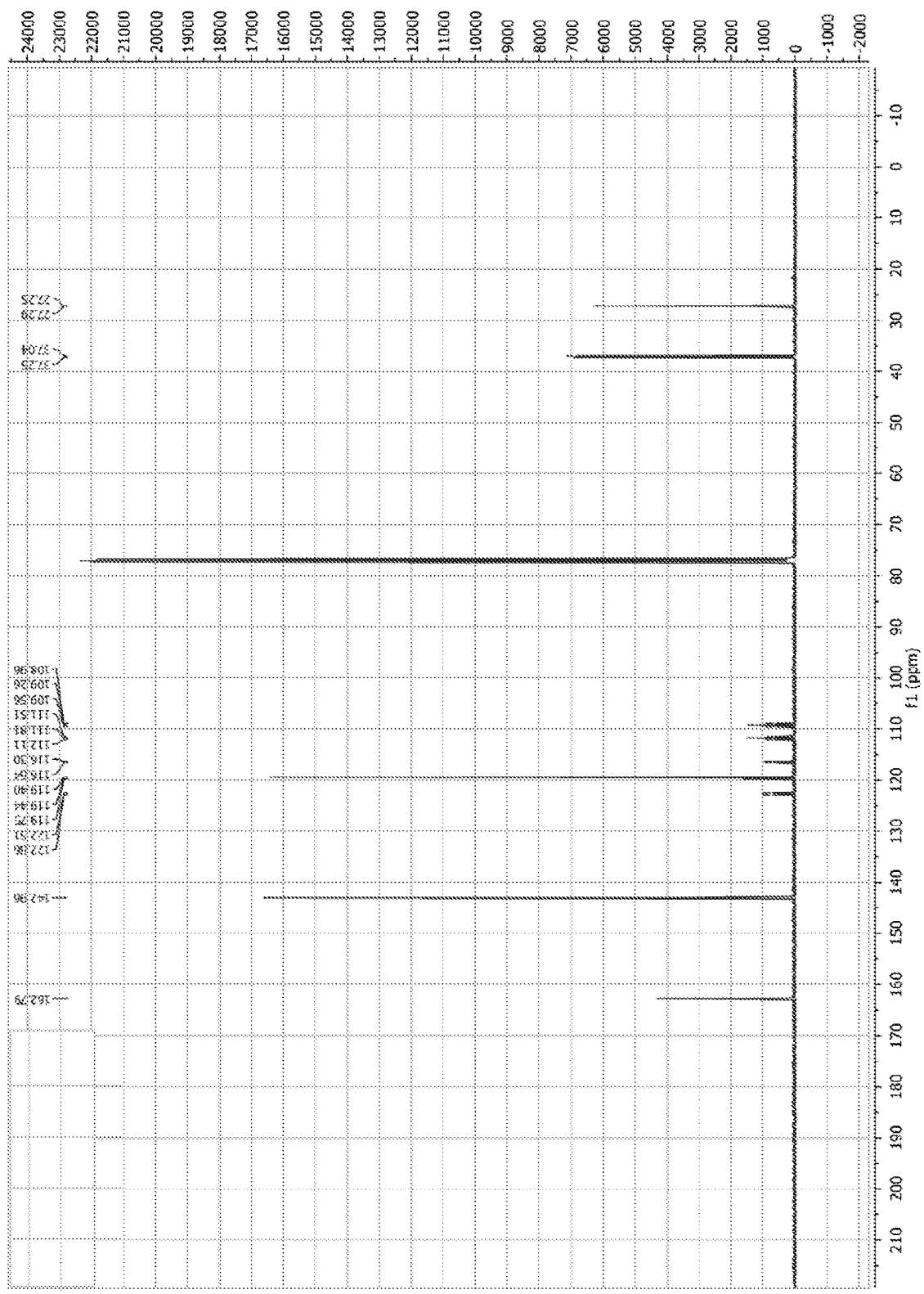
Figure 2C:
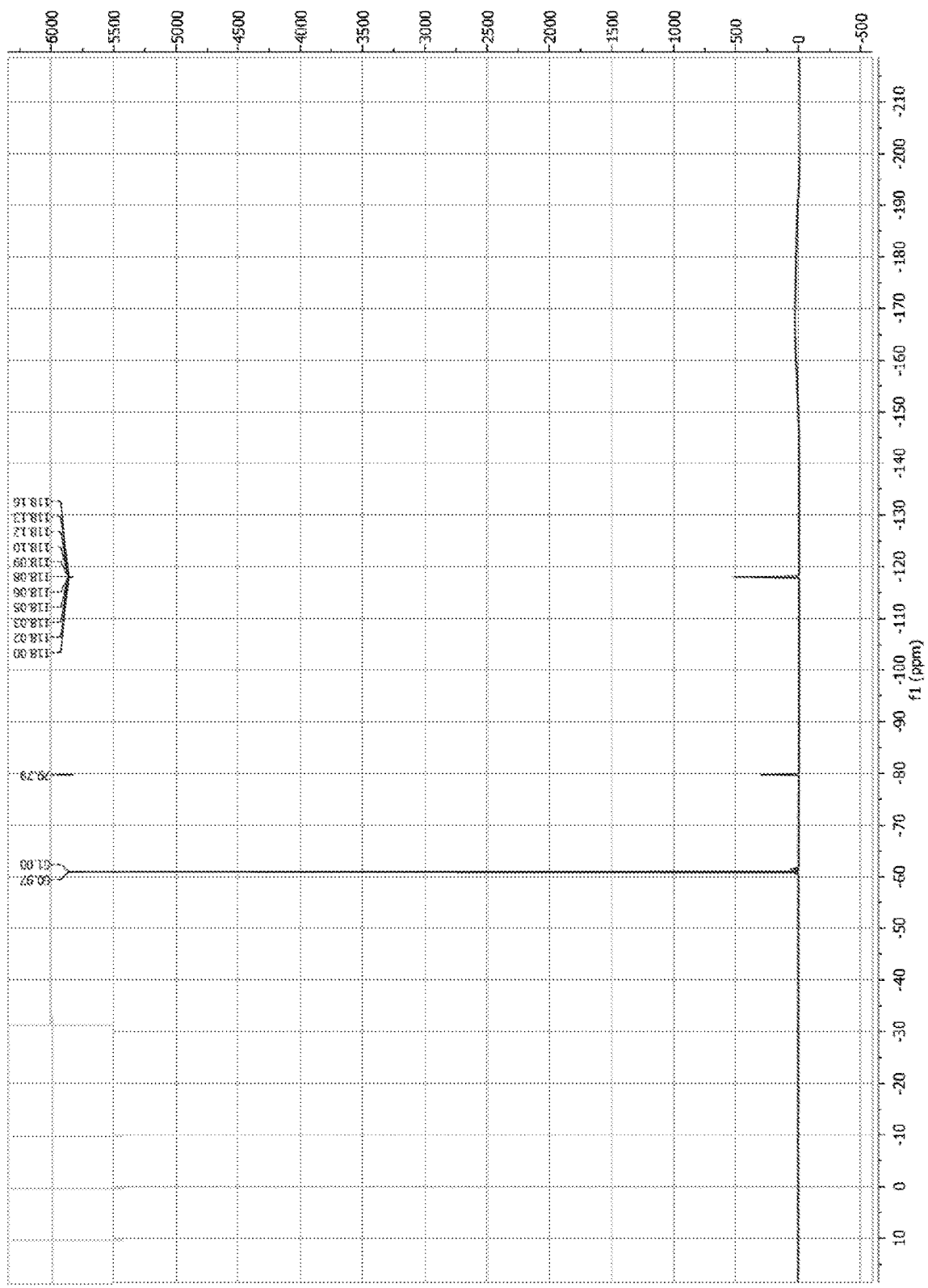

The chromatogram and mass spectrum are shown in FIGS. 1A and 1B, respectively. 1HNMR, 13CNMR and 19FNMR spectra are attached in FIGS. 2A, 2B and 2C, respectively.

The chlorination reaction was performed in 1000 ml reactor which was charged with a dried solution of Intermediate A1 in NBN obtained in Example 1 (504.0 g of a 28.0 wt. % solution in NBN). Sulfuryl chloride (70 g, added as 50% solution in NBN) was added dropwise at 25° C. over a period of 2.5 h. The addition is exothermic; a temperature rise of up to 5° C. was observed.

Upon completion of $SO_2Cl_2$ addition, the reaction mixture is stirred at ambient temperature for additional 90 min during which period the reaction mass is periodically sampled to monitor reaction progress. In case the reaction does not proceed anymore, an additional amount of $SO_2Cl_2$ needs to be added. After stirring for further 60 min the reaction is sampled periodically.

When the end of reaction has been reached, water (250 g) was added to the reaction vessel and the reaction mixture was stirred for 15 min. The reaction mixture was filtered through a filter paper. The filter paper was washed with a small amount of NBN. The filtrate was separated into aqueous and organic phases. The organic phase (~750 g) consists of 17.5 wt % of the entitled product (Intermediate B1) dissolved in NBN. Yield: ~ 84% by quantitative analysis vs. analytical standard.

The identity of Intermediate B1 was confirmed by LC-MS analysis as outlined above. Therefore, a purified sample (purified by column separation) was injected resulting in a single peak at a retention time of 11-19 min. The MS spectrum of this peak shows the expected splitting pattern of the mass peak around m/z 375.8.

Figure 3A:
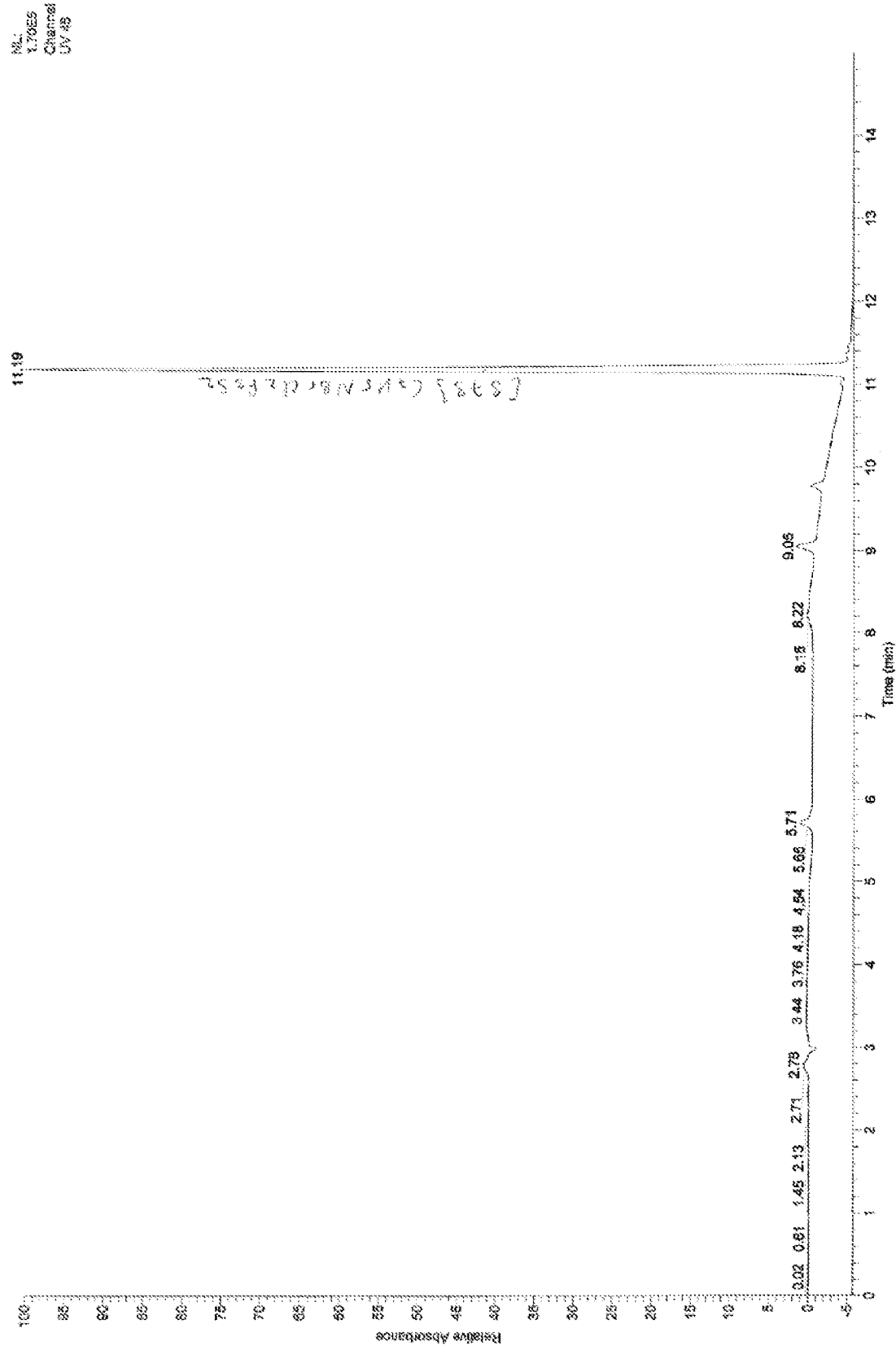
FIGS. 3A and 3B show chromatogram and mass spectrum, respectively, according to another example.
Figure 3B:
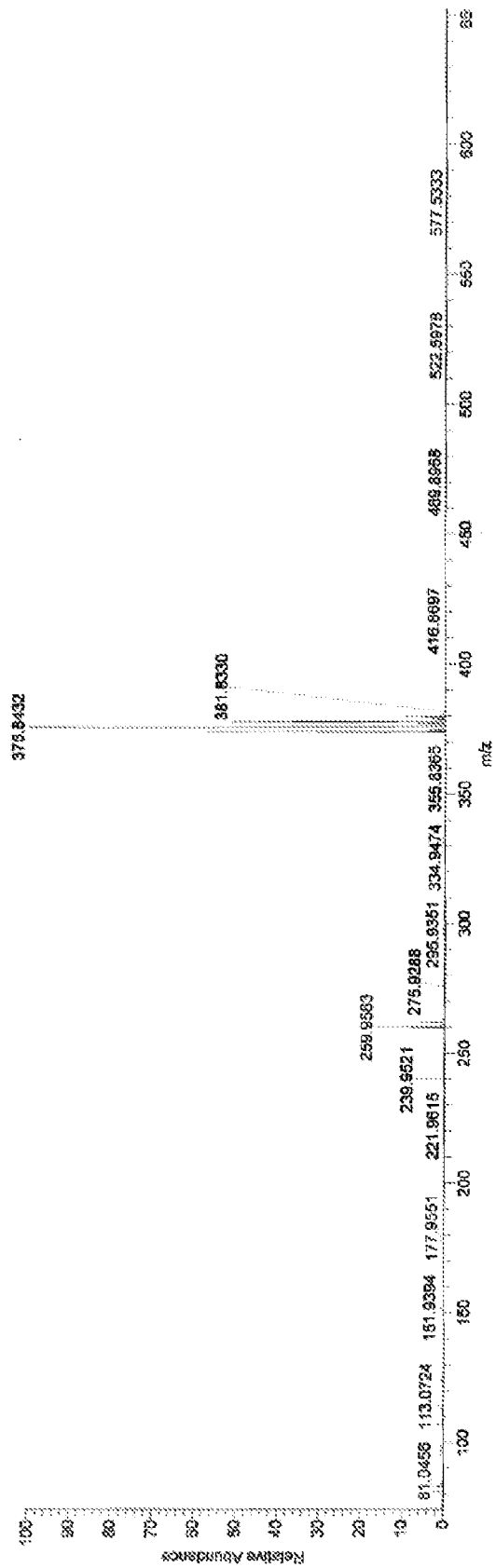
Figure 4A:
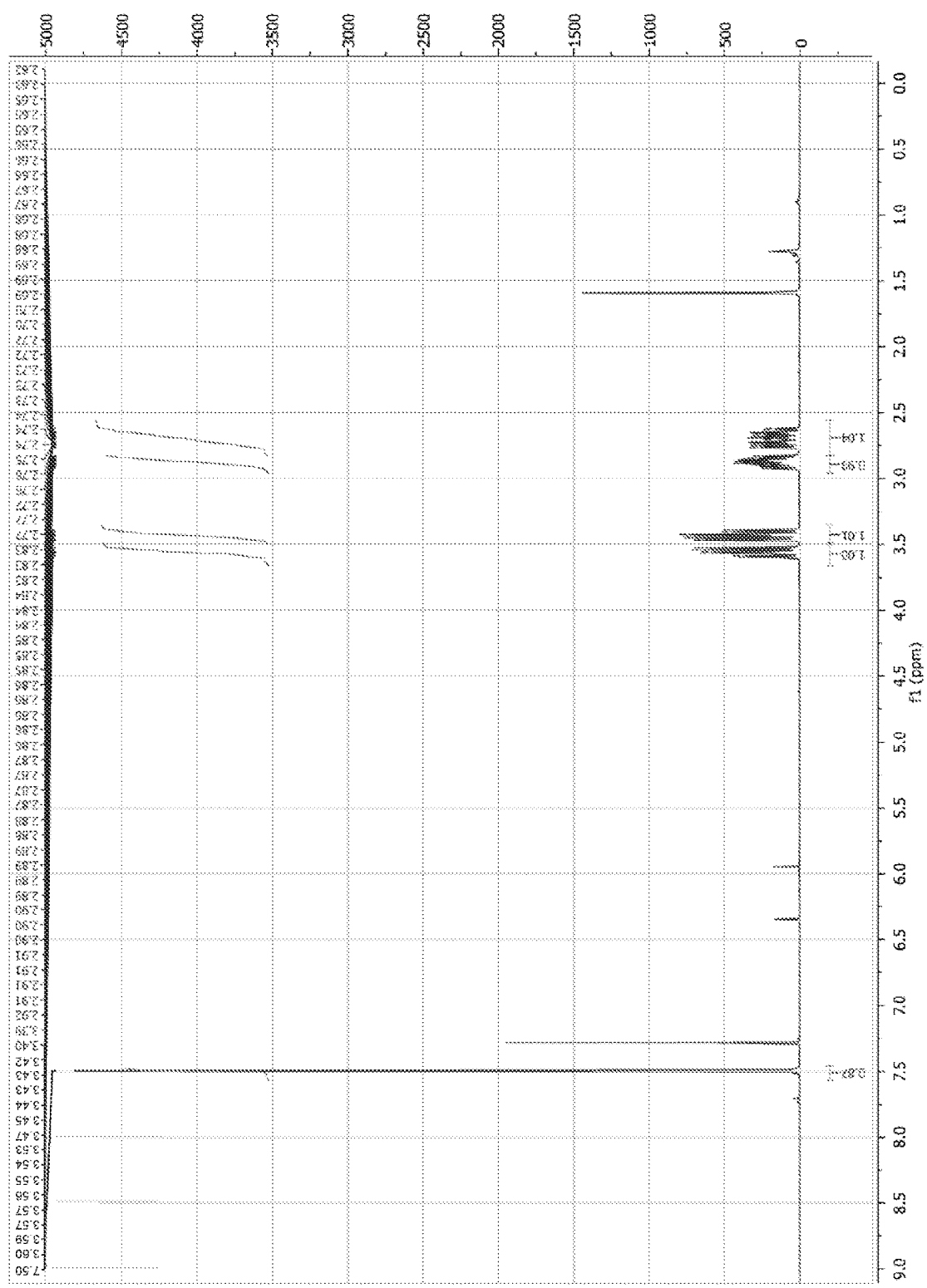
FIGS. 4A, 4B and 4C show 1HNMR, 13CNMR and 19FNMR spectra, respectively, according to another example.
Figure 4B:
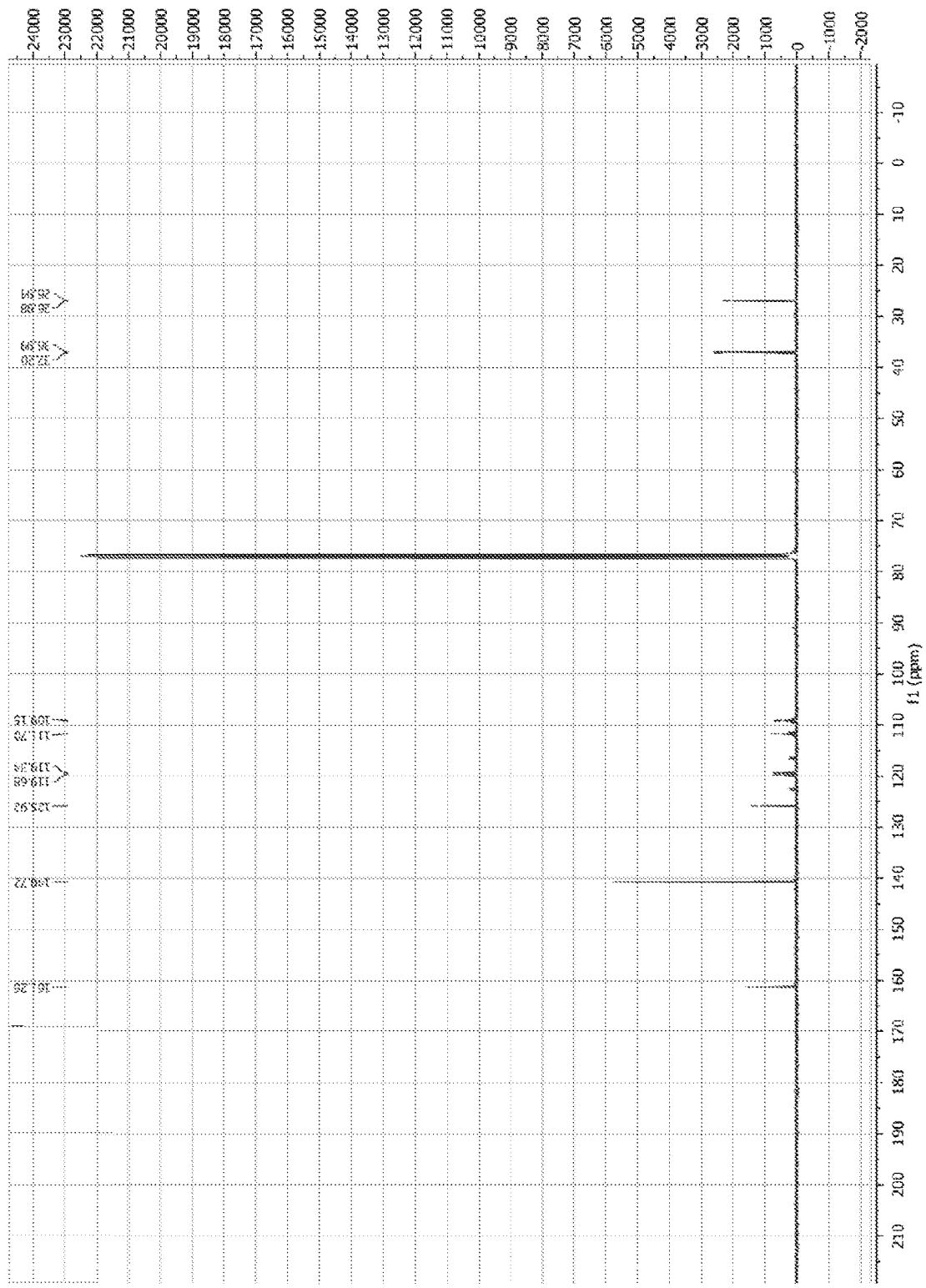
Figure 4C:
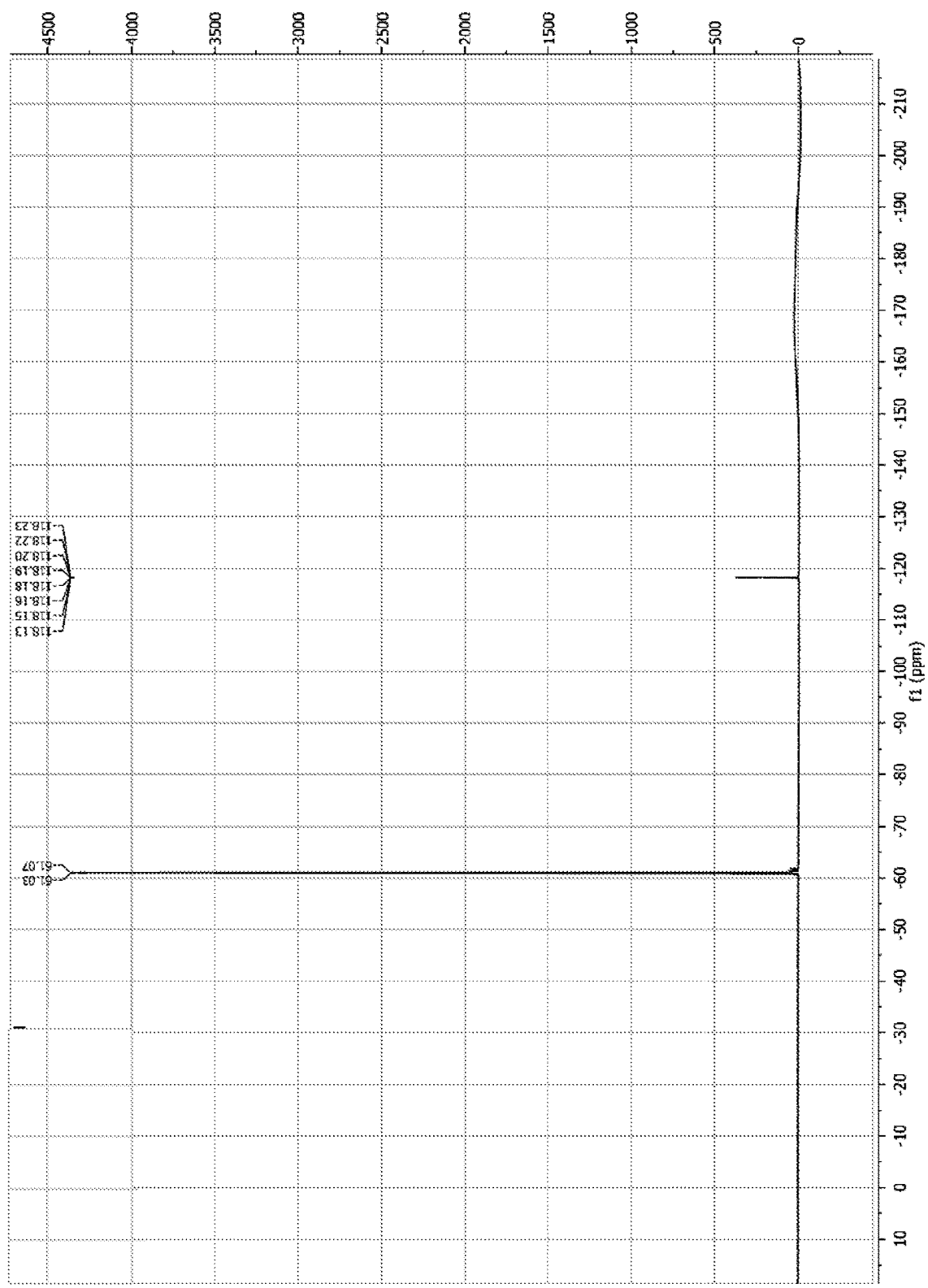

The chromatogram and mass spectrum are shown in FIGS. 3A and 3B, respectively. 1HNMR, 13CNMR and 19FNMR spectra are attached in FIGS. 4A, 4B and 4C, respectively.

Example 3 (Route 1)

Preparation of Intermediate B1 by Chlorination of Intermediate A1 Using Chlorine Gas 5-chloro-2-[(4-bromo-3-chloro-3,4,4-trifluorobutyl)thio]thiazole

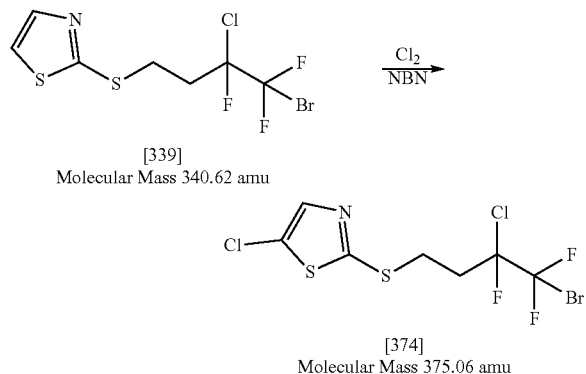

[339]
Molecular Mass 340.62 amu

[374]
Molecular Mass 375.06 amu

The chlorination reaction took place in 1 three-necked flask reactor. A solution of Intermediate A1 in NBN as obtained in Example 1 was evaporated on a rotary evaporator, then an additional co-evaporation with toluene was carried out. A distilled NBN (with water content of not more than 0.1 w/w) was added, to afford ~25 wt % solution of Intermediate A1 in NBN which was charged into the reactor. Triethylamine (0.1 eq) was added to the solution. Chlorine gas was fed to the reactor; the amount of the gas was adjusted using a calibrated bubbler. The flow rate of the gas was 0.6-0.9 mmol/min. The total amount of chlorine added was about 1.7 equivalents.

The reaction mixture was filtered through decalite using sinter Nr. 4. The organic filtrate was washed twice with 30 ml of aqueous sodium chloride solution (5 wt %). Upon accomplishing phase separation, a solution of the entitled product (Intermediate B1) in NBN is collected (24% content, indicating yield of 95% by quantitative analysis vs. analytical standard).

The LC-MS analysis of this sample was identical to the one observed in Example 2.

Example 4 (Route 1)

Preparation of Intermediate C1 from Intermediate B1 by Dehalogenation with Metal Zinc 5-chloro-2-[(3,4,4-trifluoro-3-buten-1-yl)thio]thiazole

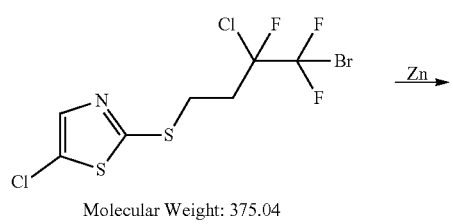

Molecular Weight: 375.04

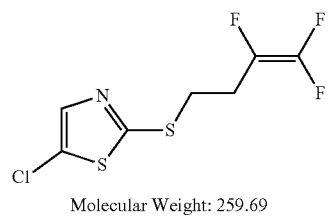

Molecular Weight: 259.69

Intermediate B1 was isolated from the NBN solution of Example 2 by evaporation of the solution on a rotary evaporator. The crude viscous material (163 g) was dissolved in methanol (100 g)

1 L reactor was charged with 140 mL methanol and 32.4 g metal zinc (zinc granules +60; available from Numinor), and heated under stirring to reach 50° C. Next, the solution of Intermediate B1 in methanol was added dropwise over 1.5 hours. After the addition was completed, the reaction mixture was refluxed and stirred for further 2 h and the mixture is periodically sampled to track the progress of the reaction.

The reaction mixture is cooled to 5° C. 1 M HCl solution is slowly added until a pH of pH<3 is obtained (under cooling). Volatiles are evaporated from the reaction mixture (MeOH). The resulting two-phase system is filtered. The organic phase is separated; the content of the entitled product is about 60 wt. %, corresponding to yields up to 85% by quantitative analysis vs. analytical standard.

Example 5

Solvent Selection for Telescopic Process

The solubility of 2-mercaptothiazole was estimated in a variety of solvents at room temperature. Large amount of 2-mercaptothiazole was added to the tested solvent. The mixture was stirred overnight. The residual solid was removed by filtration. Then the solution was analyzed by quantitative analysis vs. analytical standard to determine the concentration of the 2-mercaptothiazole. The results are recorded in Table 1.

TABLE 1

| Solvent | Solubility of 2-mercaptothiazole (wt %) |
|---|---|
| MCB (mono-chlorobenzene) | 2.4 |
| toluene | 2.2 |
| pentanol | 19.1 |
| IPAc (isopropyl acetate) | 14.8 |
| NBN (n-butyronitrile) | 28.9 |
| IBN (iso-butyronitrile) | 20.2 |
| CPME (cyclopentyl methyl ether) | 6.5 |
| 1,2-dichlorobenzene | 1.91 |
| 1,2-dichloroethane | 8.43 |

Some solvents meeting the selection criteria of creating fairly concentrated solutions (>5 wt %) of 2-mercaptothiazole were tested to determine their inertness to chlorination using either sulfuryl chloride or gaseous chlorine as chlorination reagents). Conditions of the chlorination reaction and the results—chlorination products as measured by GC analysis—are tabulated in Table 2.

TABLE 2

| | Chlorination using Cl$_2$<br>Cl$_2$ bubbling (1 mL/min) for 2 hours through 20 mL of the corresponding solvent, then sealing of the reaction vessel and stirring 8 h at room temperature | Chlorination using SO$_2$Cl$_2$<br>SO$_2$Cl$_2$ addition (~20 wt %)<br>Stirring five hours at 40° C. |
|---|---|---|
| NBN | Mono, di-chlorinated NBN, 2 Area % | Mono, di-chlorinated NBN, 0.4 Area % |
| IBN | Impurity, 3.7 Area % | Impurity, 14 Area % |
| CPME | Decomposition (more than 10 peaks) | No impurities detected |

The results indicate that NBN, IBN and CPME emerge as solvents suitable for use in a telescopic process, because they satisfy both test requirements (dissolving high concentration of 2-mercaptothiazole and being inert to at least one chlorinating agent).

Example 6 (Route 1)

Preparation of Intermediate A1 by Alkylation of Compound IV 2-[(4-bromo-3-chloro-3,4,4-trifluorobutyl)thio]thiazole

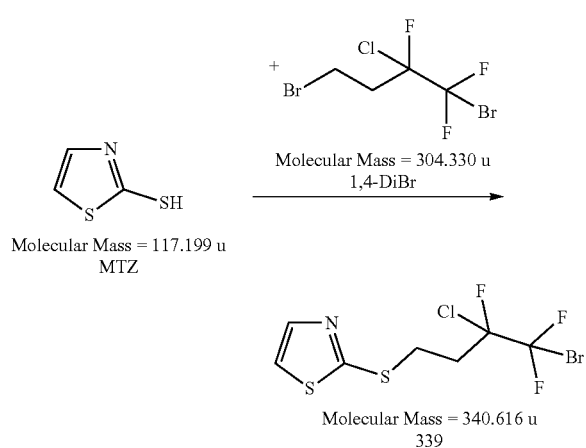

Into 1 L reactor equipped with a stirrer, reflux condenser, thermometer and pH meter was added the MTZ solution in pentanol as obtained in Preparation 2 (350 g of 14.3 wt % MTZ solution) and water (25 g), followed by dropwise addition under stirring of aqueous sodium hydroxide (45 wt %) to reach pH 4.

Next, TBAB (6.6 g) is added to the reaction mixture, followed by the addition of 1,4-DiBr (124 g). Then Na$_2$CO$_3$ was added slowly (10 g). The reaction mixture was then heated to 35° C. and aqueous sodium hydroxide solution (45 wt % solution) was added to reach pH ~8-8.5. The reaction mixture was kept under stirring for approximately one hour, during which period the reaction mixture was periodically sampled to track the progress of the reaction.

The reaction mixture was cooled to room temperature. pH was corrected to 4 with the aid of aqueous HCl solution (32 wt %). The reaction mixture was filtered. The filtrate was separated into aqueous and organic phases. The organic solvent in the organic phase, which contains the entitled product (Intermediate A1) is removed by distillation followed by top distillation of the product. 90% yield. Intermediate A1 was identified as described in Example 1.

Example 7 (Route 1)

Preparation of Intermediate B1 by Chlorination of Intermediate A1 Using SO$_2$Cl$_2$ 2-[(4-bromo-3-chloro-3,4,4-trifluorobutyl)thio]-5-chloro-1,3-thiazole

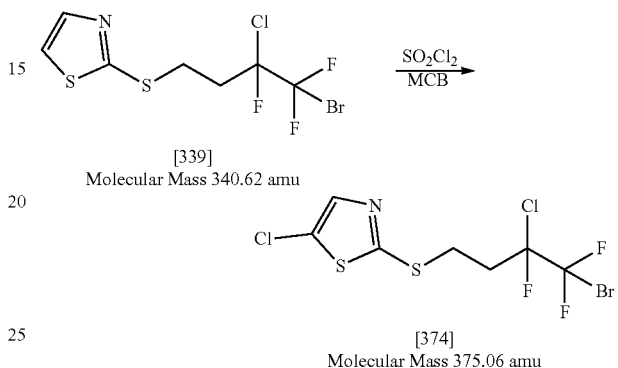

The chlorination reaction was performed in 1000 ml reactor which was charged with Intermediate A1 (100 g of 96.6% wt. %) and dry MCB 300 gr. Sulfuryl chloride (45 g) was added dropwise at 25° C. over a period of 1 h. The addition is not exothermic.

Upon completion of SO$_2$Cl$_2$ addition, the reaction mixture is stirred at 50° C. for additional 30 min during which period the reaction mass is periodically sampled to monitor reaction progress. In case the reaction does not proceed anymore, an additional amount of SO$_2$Cl$_2$ needs to be added. During stirring for further 60 min the reaction is sampled periodically.

When the end of reaction has been reached, water (200 g) was added to reaction vessel and the reaction mixture was stirred for 15 min. The phases are separated into aqueous and organic phases. The organic solvent is removed from the organic phase under reduced pressure to obtain crude product (Intermediate B1). Yield: ~ 90% by quantitative analysis vs. analytical standard. Intermediate B1 was identified as described in Example 2.

Example 8 (Route 2)

Oxidation of Intermediate B1 to Give Intermediate B2 2-[(4-bromo-3-chloro-3,4,4-trifluorobutyl)sulfonyl]-5-chloro-1,3-thiazole To 2-[(4-bromo-3-chloro-3,4,4-trifluorobutyl)thio]-5-chloro-1,3-thiazole (9.5 g, 0.025 mol, 1.0 eq.) in methanol (190 ml, 20 vol.) was added solution of Oxone® (8.56 g, 0.0278 mol, 1.1 eq.) in water (45.6 ml, 4.80 vol.) dropwise under stirring at 5° C. within 30 min. Subsequently, the white suspension was stirred at 20° C. for 1.5 hours. After this time Oxone® (0.43 g, 1.39 mmol, 0.06 eq.) was again added and the mixture was stirred for further 60 minutes. Subsequently, the mixture was again cooled to 5° C., a pH of 8-9 was adjusted with 4M NaOH and a solution of Oxone® (8.56 g, 0.0278 mol, 1.1 eq.) in water (45.6 ml, 4.80 vol) was added dropwise within 60 minutes, in which the pH was still held at 8-9. Then the mixture was stirred under pH control at 20° C. for 60 minutes. After this time Oxone® (0.26 g, 0.09 mmol, 0.033 eq.) was added once again and the mixture was stirred for a further 60 minutes.

Figure 5A:
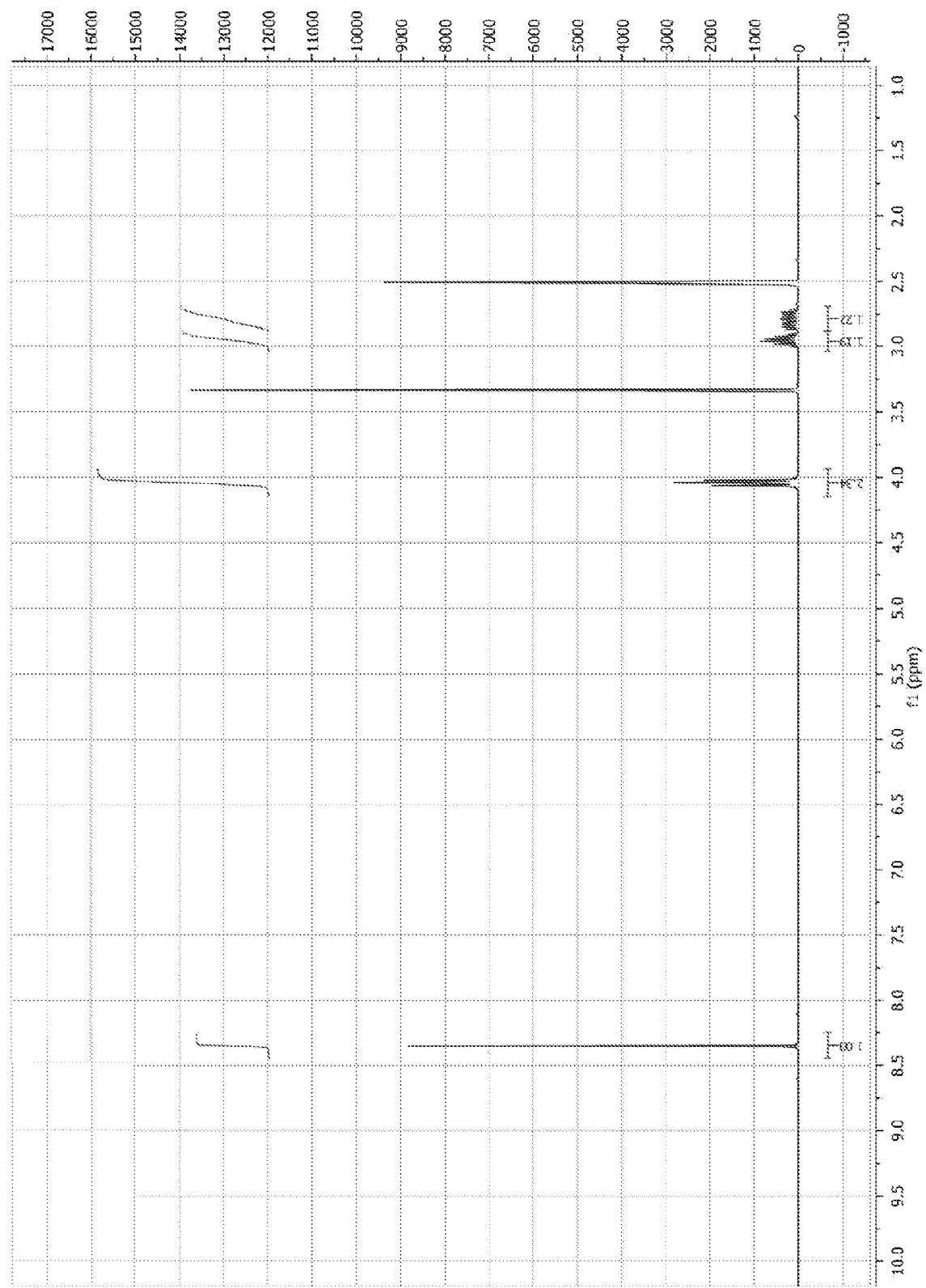
FIGS. 5A, 5B and 5C show 1HNMR, 13CNMR and 19FNMR spectra, respectively, according to yet another example.
Figure 5B:
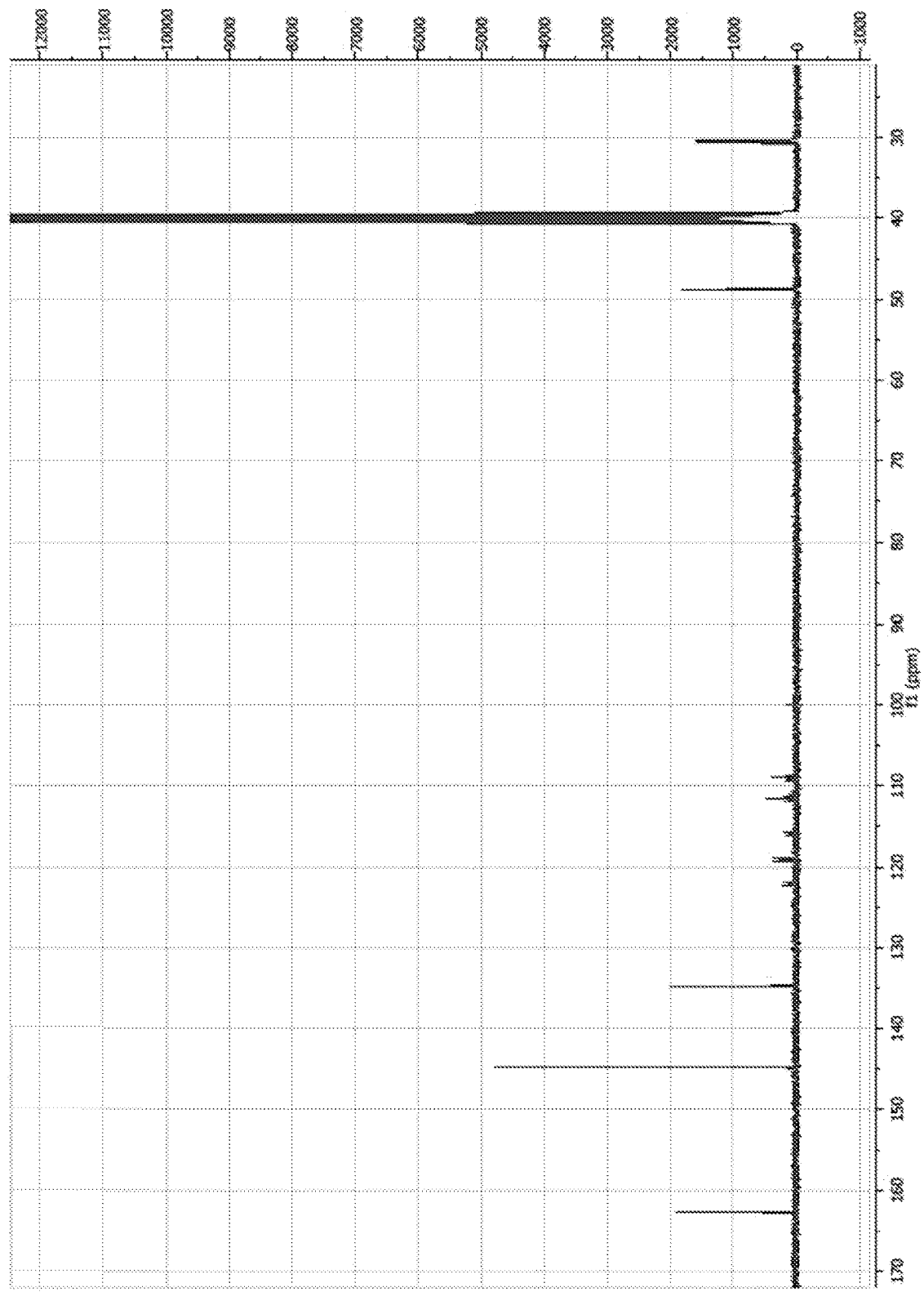
Figure 5C:
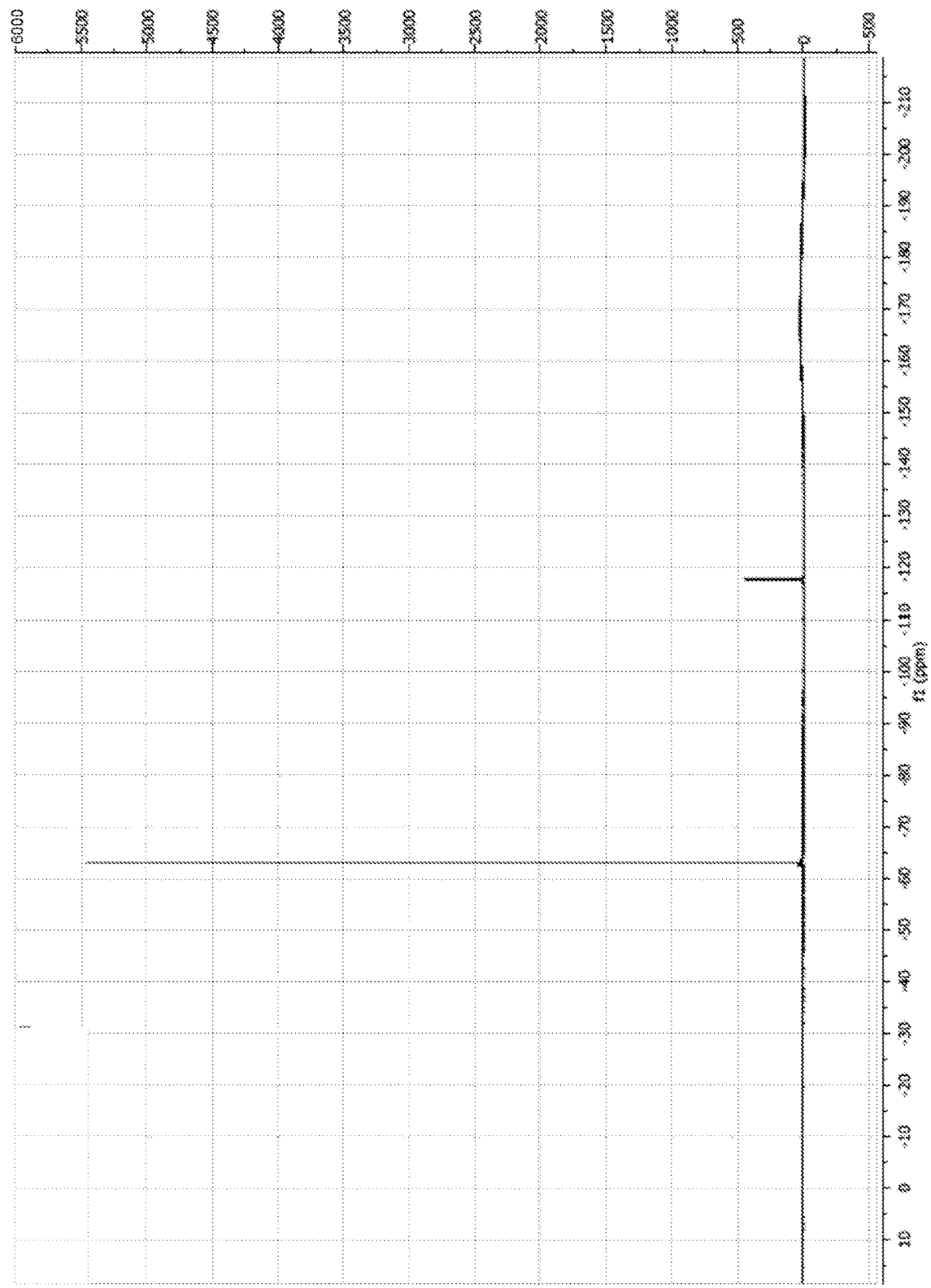

The salt was filtered off with suction, the white residue was washed twice with methanol and then the filtrate was stirred with sodium bisulfite solution (9.50 ml, 1.0 vol.). The methanol fraction was distilled from the filtrate in vacuum. Ethyl acetate was added and the organic phase was separated from the aqueous, biphasic residue and the aqueous phase was again extracted three times with ethyl acetate. The combined organic phase was dried with sodium sulphate and evaporated to give 9.7 g of the entitled product as white solid in 94% yield. LCMS and NMR confirmed the structure; 1HNMR, 13CNMR and 19FNMR spectra are attached in FIGS. 5A, 5B and 5C, respectively.

Example 9 (Route 2)

Preparation of Fluensulfone from Intermediate B2 by Dehalogenation with Metal Zinc Reaction flask was charged with zinc (powder, 2.4 g, 36.9 mmol, 3.0 eq.) and anhydrous THF (100 ml). Three drops of Br$_2$ were added and the reaction mixture was stirred for 30 minutes to activate Zn. ZnCl$_2$ (3.34 g, 24.6 mmol, 2.0 eq.) was added and the temperature was brought to reflux. 2-(4-Bromo-3-chloro-3,4,4-trifluorobutylsulfonyl)-5-chloro-1,3-thiazole (5.0 g, 12 mmol, 1.0 eq.) was then added and the reaction mixture was stirred at reflux for 24 h. After this time partial conversion was achieved according to LCMS analysis. 1 eq. (12 mmol) of ZnCl$_2$ was added and the reaction was continued for additional 7 hours. Zinc residues was then filtered off and to the filtrate 2M HCl was added followed by AcOEt. The organic layer was separated, washed with brine, dried over magnesium sulphate and concentrated under reduced pressure to give 3.7 g of the crude. To the residue Et$_2$O was added and the precipitated crystals were filtered off. The filtrate was concentrated and purified by column chromatography (100% DCM) to give pure desired product as a colorless oil in 47% yield.

The invention claimed is:

1. A process for preparing heterocyclic fluoroalkenyl sulfones and their thioether and sulfoxide precursors of the formula:

Cl—R—S(O)$_n$—(CH$_2$)$_2$—CF═CF$_2$   (Formula I')

wherein R is a heterocyclic five-membered aromatic ring and n is 0, 1 or 2, comprising a step of dehalogenation of a compound of the formula:

Cl—R—S(O)$_n$—(CH$_2$)$_2$—CFX$^1$—CF$_2$X$^2$   (Intermediate B)

wherein X$^1$ and X$^2$ are independently halogen atoms, to remove said X$^1$ and X$^2$ atoms.

2. A process according to claim 1, comprising the steps of:
A) alkylating thiol R—SH, wherein R is a heterocyclic five-membered aromatic ring, with a fluorinated haloalkane of the formula L-(CH$_2$)$_2$—CFX$^1$—CF$_2$X$^2$ in a first organic solvent, wherein L is a leaving group capable of displacement by a thiol group, and X$^1$ and X$^2$ are halogen atoms which may be the same or different, to form a thioether having the formula:

R—S—(CH$_2$)$_2$—CFX$^1$—CF$_2$X$^2$   (Intermediate A)

B) ring-chlorinating Intermediate A, optionally in a second organic solvent, to produce chlorine-substituted thioether having the formula:

Cl—R—S—(CH$_2$)$_2$—CFX$^1$—CF$_2$X$^2$   (Intermediate B)

and optionally oxidizing Intermediate B to its corresponding oxidized form Cl—R—S(O)$_n$—(CH$_2$)$_2$—CFX$^1$—CF$_2$X$^2$, wherein n is 1 or 2;

C) dehalogenation of Intermediate B or its oxidized form in a third organic solvent to remove said X$^1$ and X$^2$ atoms and produce the compound of Formula I':

Cl—R—S(O)$_n$—(CH$_2$)$_2$—CF═CF$_2$   (Formula I')

and optionally oxidizing said compound of Formula I' in case that n=0 or n=1, to afford the heterocyclic fluoroalkenyl sulfone:

Cl—R—SO$_2$—(CH$_2$)$_2$—CF═CF$_2$   (Formula I)

wherein the organic solvents used in consecutive steps are the same or different.

3. A process according to claim 2, wherein the intermediate B undergoing dehalogenation is the chlorine-substituted thioether of the formula Cl—R—S—(CH$_2$)$_2$—CFX$^1$—CF$_2$X$^2$, said process comprising:
A) alkylating thiol R—SH to give Intermediate A:

R—S—(CH$_2$)$_2$—CFX$^1$—CF$_2$X$^2$   (Intermediate A);

B) ring-chlorinating Intermediate A to produce Intermediate B:

Cl—R—S—(CH$_2$)$_2$—CFX$^1$—CF$_2$X$^2$   (Intermediate B)

C) dehalogenation of Intermediate B to remove the X$^1$ and X$^2$ halogen atoms and produce a thioether fluorinated alkene of the formula:

Cl—R—S—(CH$_2$)$_2$—CF═CF$_2$   (Intermediate C)

and optionally oxidizing Intermediate C to give the heterocyclic fluoroalkenyl sulfone:

Cl—R—SO$_2$—(CH$_2$)$_2$—CF═CF$_2$   (Formula I).

4. A process according to claim 2, wherein the thiol R—SH is 2-mercaptothiazole:

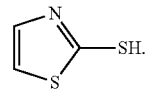

5. A process according to claim 2, wherein the fluorinated haloalkane of the formula L-(CH$_2$)$_2$—CFX$^1$—CF$_2$X$^2$ is Hal-(CH$_2$)$_2$—CFX$^1$—CF$_2$X$^2$ wherein Hal is halide.

6. A process according to claim 5, wherein the alkylation step comprises combining 2-mercaptothiazole with a fluorinated haloalkyl halide Hal-(CH$_2$)$_2$—CFX$^1$—CF$_2$X$^2$ in the first organic solvent in the presence of a base under heating, allowing the reaction to reach completion, collecting a worked-up organic solution and either isolating and optionally purifying Intermediate A from the worked-up organic solution, or carrying the Intermediate A-containing organic solution to the ring-chlorination step.

7. A process according to claim 5, wherein the fluorinated haloalkyl halide Hal-(CH$_2$)$_2$—CFX$^1$—CF$_2$X$^2$ is 1,4-dibromo-2-chloro-1,1,2-trifluorobutane.

8. A process according to claim 3, wherein the ring-chlorination reaction comprises combining Intermediate A:

R—S—(CH$_2$)$_2$—CFX$^1$—CF$_2$X$^2$   (Intermediate A)

and a chlorinating agent in the second organic solvent and recovering Intermediate B from a reaction mixture:

Cl—R—S—(CH$_2$)$_2$—CFX$^1$—CF$_2$X$^2$   (Intermediate B).

9. A process according to claim 8, wherein the chlorinating agent is selected from the group consisting of sulfuryl chloride, elemental chlorine, trichloro isocyanuric acid and N-chlorosuccinimide.

10. A process according to claim 8, wherein the Intermediate A that undergoes the ring-chlorination reaction is of the formula:

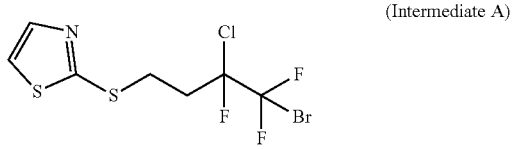 [SMILES: FC(F)(Br)C(F)(Cl)CCSc1nccs1]
(Intermediate A)

to give Intermediate B:

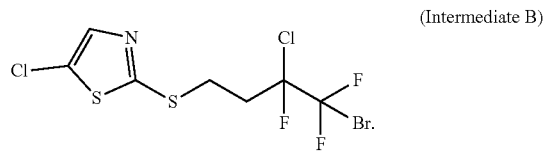 [SMILES: FC(F)(Br)C(F)(Cl)CCSc1ncc(Cl)s1]
(Intermediate B)

11. A process according to claim 1, wherein the dehalogenation reaction of Intermediate B of the formula:

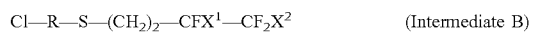
Cl—R—S—(CH$_2$)$_2$—CFX$^1$—CF$_2$X$^2$    (Intermediate B)

to remove the X$^1$ and X$^2$ halogen atoms, comprises using a reducing agent.

12. A process according to claim 11, wherein the reducing agent is a reducing metal.

13. A process according to claim 12, wherein the reducing metal is zinc.

14. A process according to claim 11, wherein Intermediate B that undergoes the dehalogenation reaction is of the formula:

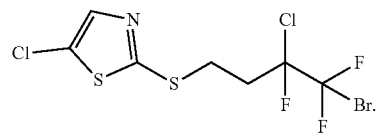 [SMILES: FC(F)(Br)C(F)(Cl)CCSc1ncc(Cl)s1]

15. A process according to claim 2, wherein the thiol used is 2-mercaptothiazole that is supplied to the alkylation step (A) in the form of a solution in the first organic solvent, said solution being a worked-up organic solution recovered following a ring closure reaction of chloroacetaldehyde with a dithiocarbamate salt in an acidic aqueous medium to give 4-hydroxy-2-thiazolidinethione, a tautomer or an isomer thereof, dehydrating same to give said 2-mercaptothiazole:

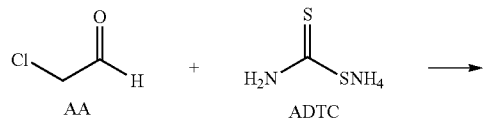

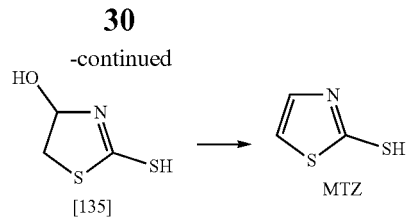

and collecting a worked-up solution of said 2-mercaptothiazole in said first organic solvent.

16. A process according to claim 15, wherein the first organic solvent is a water-immiscible organic solvent that meets the requirements:
1) The solubility of 2-mercaptothiazole in the first solvent at 25° C. is not less than 5 wt %; AND
2) The solvent is sufficiently inert to at least one chlorinating reagent.

17. A process according to claim 16, comprising the steps of collecting, after the alkylation step has been completed, a worked-up solution of

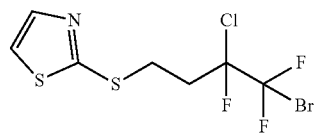 [SMILES: FC(F)(Br)C(F)(Cl)CCSc1nccs1]

in the first organic solvent and carrying said worked-up solution to the ring-chlorination step, such that the first and second organic solvents are identical, whereby the synthesis of 2-mercaptothiazole and subsequent alkylation and chlorination reactions are telescoped.

18. A process according to claim 17, wherein the first organic solvent is selected from the groups consisting of aliphatic nitriles and ethers of the formula R1-O—R2, wherein R1 is aliphatic ring and R2 is straight or branched alkyl.

19. A process according to claim 18, wherein the first organic solvent is an aliphatic nitrile which is n-butyronitrile.

20. A process according to claim 15, wherein the first organic solvent is C4-05 water-immiscible alkanol, the process comprises steps of isolation of the alkylation product and solvent exchange to a second organic solvent prior to the chlorination reaction.

21. A process according to claim 20, wherein the water immiscible alkanol is 1-pentanol, which is exchanged for halogenated aromatic hydrocarbon prior to chlorination.

22. A process according to claim 3, further comprising oxidizing Intermediate C.

23. A process according to claim 1, wherein Fluensulfone is prepared:

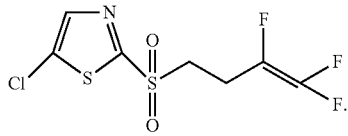 [SMILES: O=S(=O)(CCC(F)=C(F)F)c1ncc(Cl)s1]

24. A process according to claim 2, wherein the oxidized form of intermediate B of the formula Cl—R—SO$_2$—(CH$_2$)$_2$ —CFX$^1$—CF$_2$X$^2$ undergoes dehalogenation, said process comprising:

A) alkylating thiol R—SH to give the thioether

R—S—(CH$_2$)$_2$—CFX$^1$—CF$_2$X$^2$   (Intermediate A);

B) ring-chlorinating Intermediate A to produce chlorine-substituted thioether compound of the formula:

Cl—R—S—(CH$_2$)$_2$—CFX$^1$—CF$_2$X$^2$   (Intermediate B);

C) oxidizing Intermediate B to produce the corresponding oxidized form of Intermediate B, which is sulfone of the formula:

Cl—R—SO$_2$—(CH$_2$)$_2$—CFX$^1$—CF$_2$X$^2$

D) dehalogenation of said oxidized form of Intermediate B to give the heterocyclic fluoroalkenyl sulfone:

Cl—R—SO$_2$—(CH$_2$)$_2$—CF=CF$_2$   (Formula I), wherein organic solvents used in consecutive steps are the same or different.

25. A process according to claim 24, wherein the intermediate B which undergoes oxidation is:

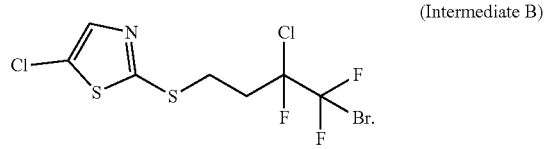 [SMILES: FC(F)(Br)C(F)(Cl)CCSc1ncc(Cl)s1]
(Intermediate B)

26. A process according to claim 24, wherein Intermediate B is oxidized with the aid of an oxidizing agent consisting of the mixture KHSO$_5$.0.5KHSO$_4$.0.5K$_2$SO$_4$.

27. A process according to claim 26, comprising progressively adding the reagent KHSO$_5$.0.5KHSO$_4$.0.5K$_2$SO$_4$ to a reaction vessel that was previously charged with alkanol and the intermediate B1.

28. A process according claim 25, wherein the oxidized form of Intermediate B which undergoes dehalogenation is:

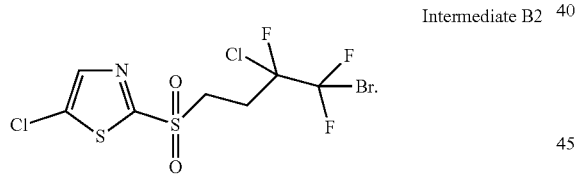
Intermediate B2

29. A process according to claim 24, wherein the dehalogenation reaction comprises using a reducing metal.

30. A process according to claim 29, comprising using zinc in tetrahydrofuran, with in-situ activation of said zinc.

31. A compound of the formula

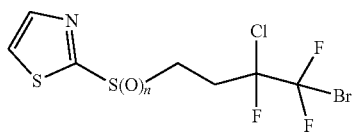

wherein n=0, 1 or 2, or an acid addition salt thereof.

32. A compound according to claim 31 wherein n=0:

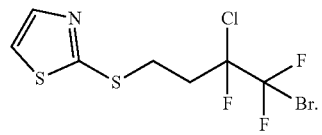 [SMILES: FC(F)(Br)C(F)(Cl)CCSc1nccs1]

33. A compound of the formula:

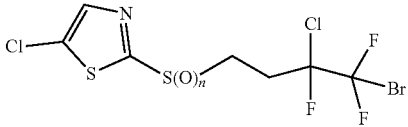

wherein n=0, 1 or 2, or an acid addition salt thereof.

34. A compound according to claim 33 wherein n=0:

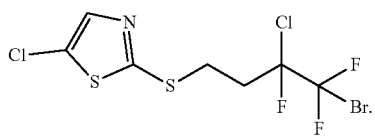 [SMILES: FC(F)(Br)C(F)(Cl)CCSc1ncc(Cl)s1]

35. A compound according to claim 33 wherein n=2:

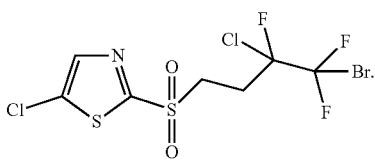 [SMILES: O=S(=O)(CCC(F)(Cl)C(F)(F)Br)c1ncc(Cl)s1]

* * * * *